(12) United States Patent
Luo et al.

(10) Patent No.: US 11,434,288 B2
(45) Date of Patent: Sep. 6, 2022

(54) NUCLEOLIN-MEDIATED CANCER DIAGNOSTICS AND THERAPY

(75) Inventors: Yongzhang Luo, Beijing (CN); Hubing Shi, Beijing (CN)

(73) Assignees: Protogen Ltd., Beijing (CN); Tsinghua University, Beijing (CN)

( * ) Notice: Subject to any disclaimer, the term of this patent is extended or adjusted under 35 U.S.C. 154(b) by 39 days.

(21) Appl. No.: 12/412,065

(22) Filed: Mar. 26, 2009

(65) Prior Publication Data

US 2009/0191224 A1 Jul. 30, 2009

Related U.S. Application Data

(62) Division of application No. 11/193,042, filed on Jul. 29, 2005, now abandoned.

(30) Foreign Application Priority Data

May 12, 2005 (CN) .......................... 200510011707.3

(51) Int. Cl.
| | | |
|---|---|---|
| *G01N 33/574* | (2006.01) | |
| *A61K 38/39* | (2006.01) | |
| *C07K 16/28* | (2006.01) | |

(52) U.S. Cl.
CPC ....... *C07K 16/28* (2013.01); *G01N 33/57492* (2013.01); *C07K 2317/73* (2013.01); *C07K 2317/76* (2013.01); *C07K 2317/77* (2013.01)

(58) Field of Classification Search
CPC combination set(s) only.
See application file for complete search history.

(56) References Cited

U.S. PATENT DOCUMENTS

| | | |
|---|---|---|
| 7,078,485 B2 | 7/2006 | Luo et al. |
| 9,320,810 B2 * | 4/2016 | Ruoslahti ............... A61K 47/64 |
| 2003/0120428 A1 | 6/2003 | Masaki et al. |
| 2003/0194754 A1 | 10/2003 | Miller et al. |
| 2004/0186056 A1 | 9/2004 | Ruoslahti et al. |
| 2005/0053607 A1 * | 3/2005 | Bates ...................... A61P 35/00 424/155.1 |
| 2006/0058232 A1 * | 3/2006 | Luo et al. ....................... 514/12 |

FOREIGN PATENT DOCUMENTS

| | | |
|---|---|---|
| EP | 1912066 A1 | 4/2008 |
| WO | 00/32631 A2 | 6/2000 |
| WO | 03/086174 A2 | 10/2003 |
| WO | WO 03/087124 * | 10/2003 |
| WO | 03/092737 A1 | 11/2003 |
| WO | 2004/091383 A2 | 10/2004 |
| WO | 2004/104227 A1 | 12/2004 |
| WO | 2005/035579 A1 | 4/2005 |

OTHER PUBLICATIONS

Christian et al (J Cell Biology, 2003, 163:871-878).*
Christian et al (Journal of Cell Biology, 2003, 163:871-878).*
Office Action of CA Application No. 2,607,832 dated Mar. 12, 2010.
Office Action of AU Application No. 2006246197 dated Jan. 25, 2010.
Office Action of AU Application No. 2010241351 dated Jun. 13, 2011.
Supplementary European Search Report for EP 062240 dated Sep. 8, 2008.

* cited by examiner

*Primary Examiner* — Laura B Goddard
(74) *Attorney, Agent, or Firm* — Millen, White, Zelano & Branigan, PC; Diana Hamlet-Cox

(57) ABSTRACT

The present invention provides for diagnostic kits for identifying cancer patients who are more susceptible to cancer therapies employing endostatin and other angiogenesis inhibitors, based upon the discovery that Nucleolin is a specific receptor for Endostatin. In particular, the diagnostic kits include antibody molecules against Nucleolin, DNA or RNA molecules that specifically bind to nucleic acid molecules encoding Nucleolin. The present invention also discloses methods of screening for angiogenesis inhibitors which specifically interact with Nucleolin, and act as angiogenesis inhibitors in an analogous manner as Endostatin. In addition, the present invention discloses methods of inhibiting the proliferation of endothelial cells or angiogenesis of tumor by administering an anti-nucleolin antibody linked to a cytotoxic agent such as tumor necrosis factor alpha to the endothelial cells.

15 Claims, 22 Drawing Sheets c

| IP: | NL | |
|---|---|---|
| IB: | ES | |
| Heparin: | 0 nM | 200 nM |
| NL: | 20 nM | 20 nM |
| ES: | 20 nM | 20 nM |

20.1 kDa-- ←ES

FIG. 2E e

| | | |
|---|---|---|
| IP: | | NL |
| IB: | | ES |

Incubation time (min): Control 30 60 120

20.1 kDa-- ←ES 43 kDa-- ←β-actin

FIG. 2F-I
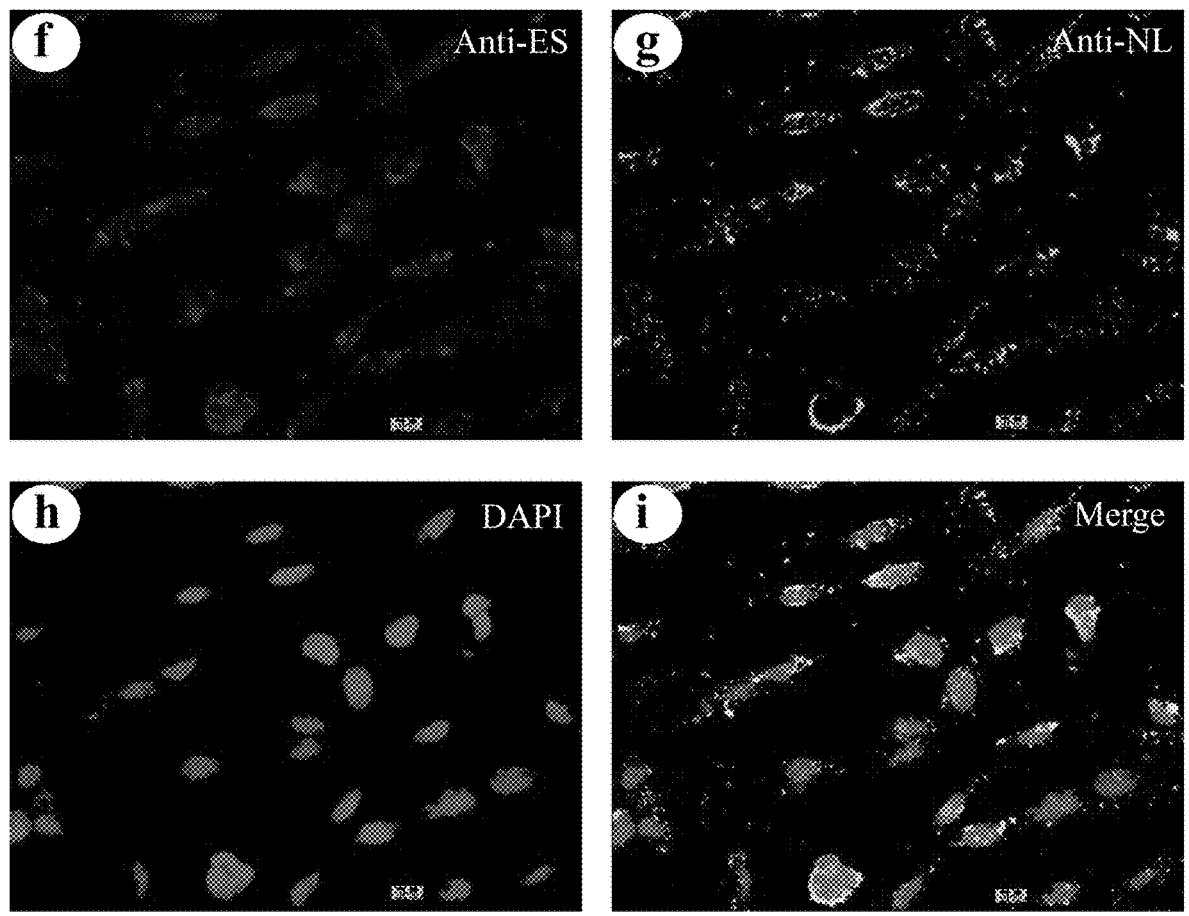

e

| | BS/U6 | BS/U6/263 | BS/U6/1356 |

NL

Myosin

FIG. 4A-G
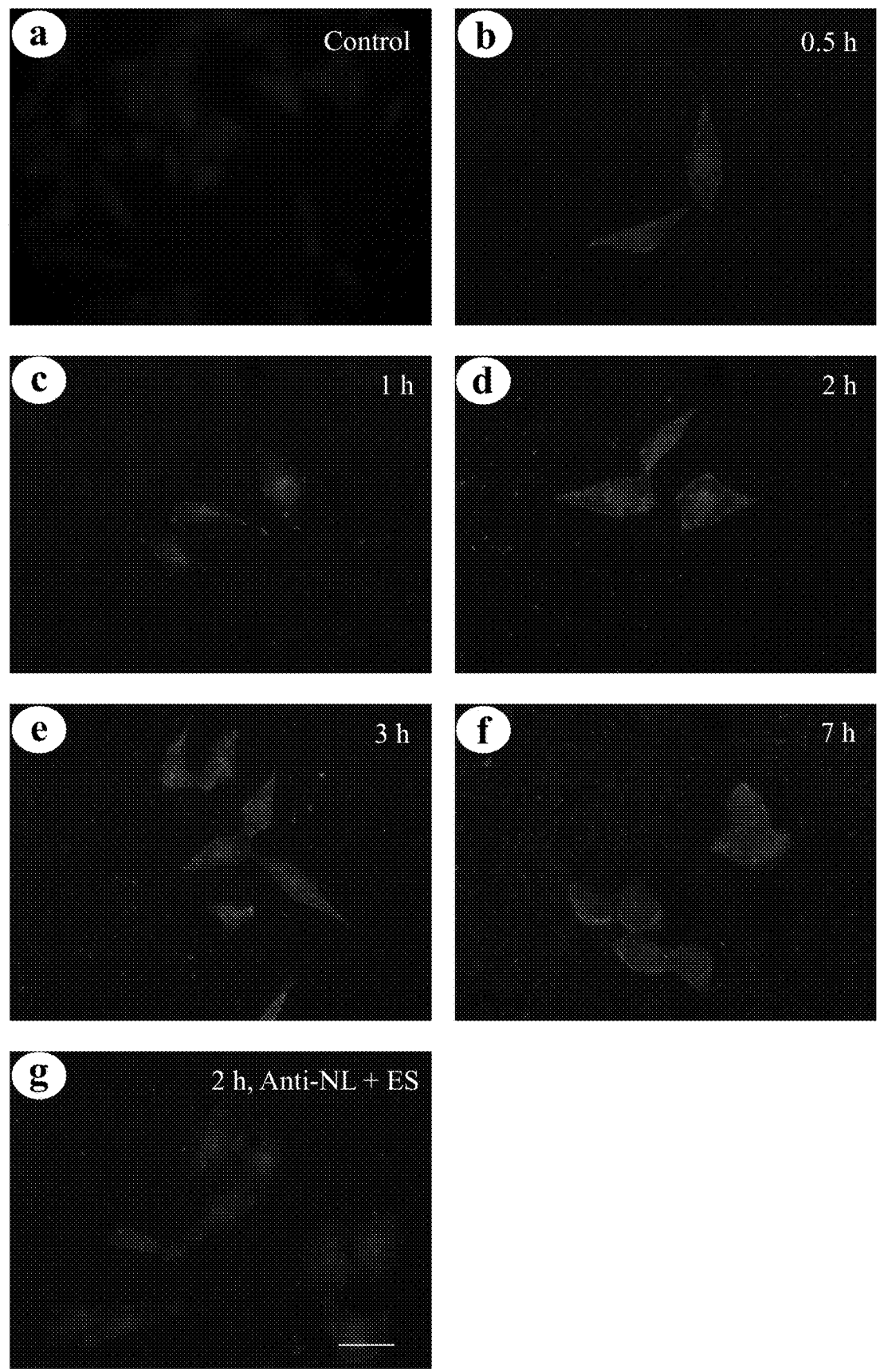

h

| VEGF: | − | − | − | + | + |
| bFGF: | − | + | + | − | − |
| ES:   | − | − | + | − | + |

97.4 kDa—     ←NL

IB:       NL 97.4 kDa—     ←NL

FIG. 4I-K
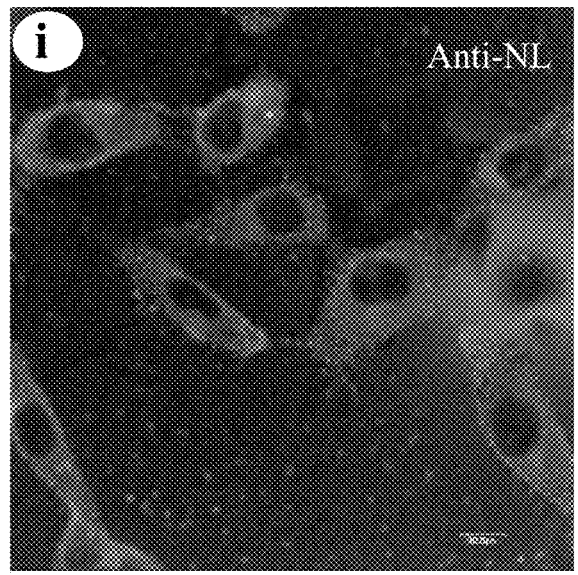
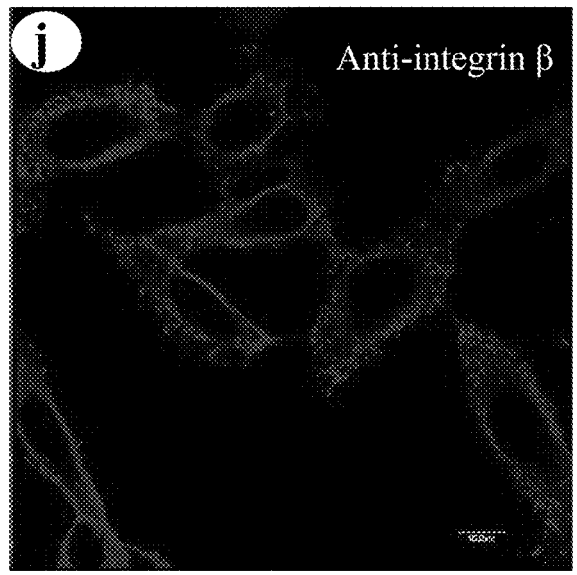
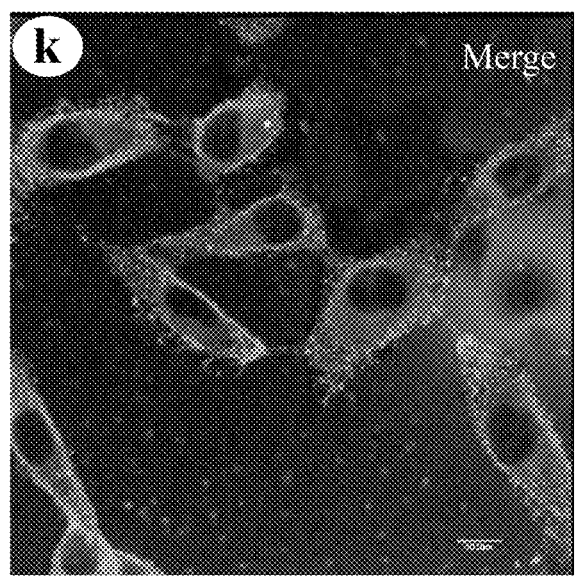

FIG. 5A-F
Proliferating cells | Quiescent cells
 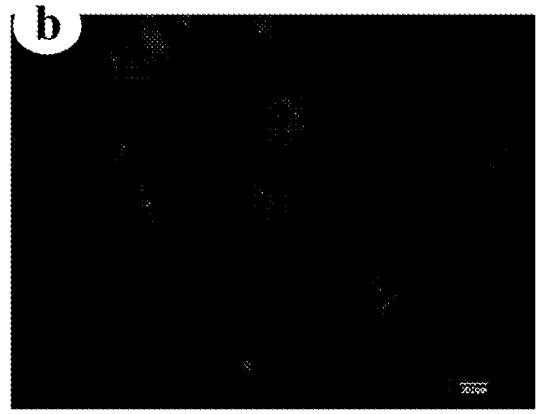
Anti-NL
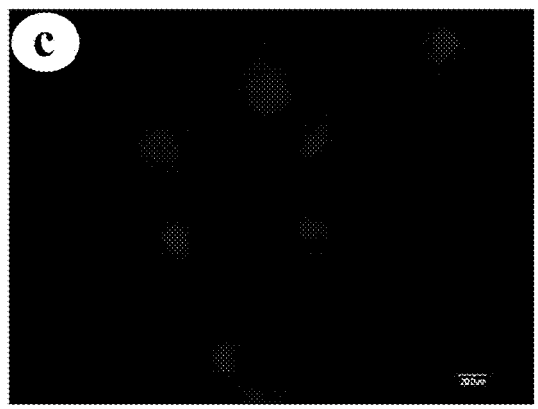 
DAPI
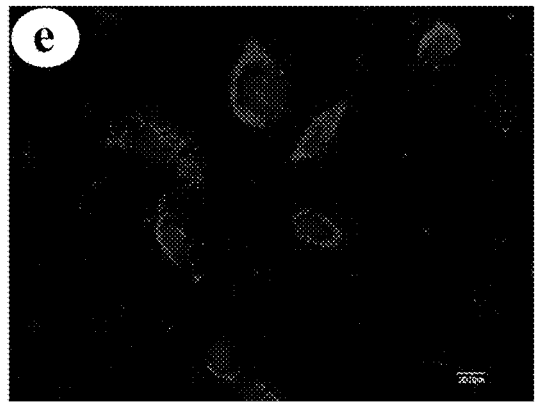 
Merge

NUCLEOLIN-MEDIATED CANCER DIAGNOSTICS AND THERAPY

CROSS REFERENCE TO RELATED APPLICATIONS

This application is a divisional of application Ser. No. 11/193,042, filed Jul. 29, 2005, now abandoned, which claims priority to Chinese Patent Application Serial No. 200510011707.3, filed May 12, 2005. The entire disclosures of the prior applications are incorporated herein by reference.

BACKGROUND OF THE INVENTION

Field of the Invention

The present invention relates to a novel method of identifying cancer subjects, in particular human patients, who are suitable candidates for anti-angiogenesis cancer therapy. The present invention also relates to a novel approach in searching and screening for angiogenesis inhibitors, molecules which are believed to be effective in reducing the malignant growth of cells, particularly in those cancers which are angiogenesis-dependent. The present invention discloses methods of screening for inhibitors of angiogenesis using the molecule nucleolin. In particular, the present invention relates to screening for angiogenesis inhibitors which functions in a manner that is analogous to the protein endostatin. The invention is based upon the discovery that nucleolin is a specific receptor for endostatin, and is involved in the signal transduction pathway of endostatin when it functions as an angiogenesis inhibitor.

Description of Related Art

The effectiveness of cancer therapy can vary greatly among targeted patients depending upon a variety of factors, both external and internal. External factors include the different stages of the cancer at the time of treatment, where early detection is key to effective treatment and recovery, the relevant strength of the cancer therapy, such as surgery, chemotherapy, or radiation therapy. Internal factors include the health of the immune system of the patient, where a strong system can sustain a longer and stronger regiment of treatment, and thus helping the patient recover faster. A key issue that is being explored in the cancer therapy, and in medicine in general, in what's called personalized medicine. The notion that different individuals may have different tolerance and susceptibility to the same cancer drug or therapy has inspired a variety of approaches in the effort to increase the efficacy of a particular cancer therapy. Thus, due to individual variations, a drug that is effective on one patient may not be so on another.

In the field of cancer therapy, attempts have been made to use gene profiling to understand whether a particular drug can exert its therapeutic function effectively on a patient with a particular genetic profiling. One approach of cancer therapy discovered recently has been using endostatin to inhibit the angiogenesis of tumor cells, and thus inhibiting the growth of tumor by stopping blood supply to the tumors. To understand the individualized application of endostatin therapy, recently, there have been attempts to use gene microarray to study the gene expression profiling underlying the inhibitory effects of endostatin on angiogenesis of endothelial cells. See M. Mazzanti, et al., Genome Research, 14:1585-1593 (2004).

In the context of endostatin cancer therapy, endostatin has been hailed as an effective cancer therapy because it works to kill cancer cells by inhibiting angiogenesis, a process which is required by the cancer cells in order to metastasize. Every increase in the tumor cell population must be preceded by an increase in new capillaries that converge upon the tumor. This phenomenon is nearly universal; most of the human solid tumors and hematopoietic malignancies are angiogenesis dependent. Additional advantages to antiangiogenic therapy include low toxicity, minimal drug resistance, and repeated cycles of antiangiogenic therapy may be followed by a prolonged tumor dormancy without further therapy. See Boehm et al., Antiangiogenic therapy of experimental cancer does not induce acquired drug resistance. Nature (1997) 390: 404-407. However, so far the mechanism of function of how endostatin works is still not clear. Therefore, endostatin therapy is being applied to cancer patients across the board without referencing to each patient's susceptibility of the therapy. Numerous clinical trials have been conducted in hope of finding an effective drug for anti-angiogenesis. It would be a significant progress if patients can be selected using objective criteria so they can be treated more effectively with endostatin. This invention discloses methods and diagnostic kits directed to this endeavor.

SUMMARY OF INVENTION

The present invention provides a kit for determining the susceptibility of a subject to endostatin cancer therapy, comprising a label that labels nucleolin and a usage instruction for performing a screening of a sample of said subject with said label such as that an amount of nucleolin present in the sample is determined. Preferably, the subject is a mammal. More preferably, the subject is a human. In certain preferred embodiment of the invention, the nucleolin being labeled is cell surface nucleolin. In other embodiment of the invention, the label comprises an antibody that specifically binds to nucleolin, preferably a polyclonal antibody, and more preferably, a monoclonal antibody. In yet another embodiment of the invention, the label comprises a nucleic acid molecule, or probe, preferably a DNA probe, and still preferably, an RNA probe.

The present invention further provides a method of determining the likelihood of success of endostatin cancer therapy in a subject, comprising screening a sample from said subject for the level of expression of nucleolin, and determining if said subject is susceptible to endostatin cancer therapy based on the amount of nucleolin expression.

The present invention provides methods of screening for angiogenesis inhibitors, in particular, molecules which function in a similarly manner as endostatin. The invention provides methods of using Nucleolin, referred to herein as "NL", as a target molecule, applying conventional methodologies, candidate molecules can be examined so as to uncover those molecules that bind specifically to NL, at the same time, exhibiting angiogenesis activities. Due to the fact that NL is a specific cell surface receptor for endostatin, the new molecules discovered in the manner described above should function in a similarly manner as endostatin.

The present invention also provides methods of enhancing the sensitivity of target endothelial cells to endostatin. The methods herein provide introducing exogenous NL molecules into the target endothelial cells, such that the NL molecules are over-expressed as compared to their wild type levels. Preferably, these target cells are those that normally do not express a high level NL endogenously. The methods further provide the introduction of NL to targeted endothelial cells, such that these modified cells can be effectively killed by endostatin due to endostatin's angiogenesis properties. The present invention also provides for antibodies against NL molecules, which can be used to detect target cancer cells having a high level of surface NL and as such are good candidate for ES cancer therapy.

In one embodiment, the present invention provides a method of producing an NL-specific angiogenesis inhibitor effective in inhibiting angiogenesis, comprising: applying an appropriate binding assay to a pool of candidate molecules, thereby obtaining a plurality of NL-specific molecules; testing each of the plurality of NL-specific molecules for its effectiveness of inhibiting angiogenesis using an anti-angiogenesis assay; and selecting the resulting NL-specific molecule which is effective in inhibiting angiogenesis as demonstrated by the anti-angiogenesis assay.

In another embodiment, the present invention provides a method of selecting an angiogenesis inhibitor having the ability to inhibit endothelial proliferation when added to proliferating endothelial cells in vitro, comprising the steps of: using a pharmaceutically acceptable method to discover molecules that specifically interact with NL as the target molecule; testing the molecules thus derived from the previous step for their effectiveness in inhibiting endothelial cell proliferation or migration; and harvesting the molecule thus derived which are effective in inhibition of endothelial cell proliferation or migration, wherein the effectiveness of the anti-angiogenesis function of said molecule is compared to that of Endostatin.

In a further embodiment, the present invention provides a method of increasing the receptiveness of a target cell to an angiogenesis inhibitor, comprising: introducing exogenous NL into the target cells, thereby obtaining a plurality of modified target cells expressing exogenous NL, and measuring the killing rate of the modified target cells by endostatin.

In another embodiment, the present invention provides a method of enhancing the anti-angiogenesis effect of an angiogenesis inhibitor on a target endothelial cell, comprising introducing into said target cell a pharmaceutically effective amount of exogenous NL molecule, said NL molecule being able to express in said target cell; and incubating said target cell with said angiogenesis inhibitor, thereby causing the inhibition of the growth of said target cell.

In one embodiment, the present invention provides a method of increasing the efficacy of angiogenesis inhibitors on controlling the growth of a cancer in a patient having such cancer, comprising identifying the presence of the level of endogenous NL molecules in a sample of the cancer of said patient, using acceptable methods; and determining the likelihood of efficacy of angiogenesis inhibitor on said cancer patient using the level of expression of NL in said patient, a higher level of NL indicating a higher degree of success of such angiogenesis inhibitor treatment. Preferably, the angiogenesis inhibitor is endostatin.

In another embodiment, the present invention provides a diagnostic kit for assaying the individual sensitivity of target cells towards angiogenesis inhibitors, comprising a molecule that specifically bind to an NL molecule; and a pharmaceutically acceptable carrier. Preferably, the molecule is a polyclonal antibody, and more preferably, the antibody is a monoclonal antibody.

In a further embodiment, the present invention provides a method of identifying target cancer cells which are susceptible to an anti-angiogenesis inhibitor treatment, comprising generating an anti-nucleolin antibody; using said anti-nucleolin antibody to screen a sample of said target cancer cells; and identifying target cancer cells susceptible to anti-angiogenesis inhibitor treatment as indicated by the specific interactions between the target cancer cells and the anti-nucleolin antibody. Preferably, the antibody is a polyclonal antibody, and more preferably, the antibody is a monoclonal antibody.

In yet another embodiment, the present invention provides a diagnostic kit for determining the target cancer cells which are susceptible to anti-angiogenesis inhibitor treatment, comprising an antibody against nucleolin and a pharmaceutically acceptable carrier.

In yet another embodiment, the present invention provides a diagnostic kit for determining and selecting cancer subjects which are susceptible to anti-angiogenesis inhibitor treatment, comprising a label that is capable of binding to nucleolin and indicating its presence, and a written instruction for performing a screening test of a sample of the cancer subject such that the level of presence of nucleolin is detected in the sample.

DETAILED DESCRIPTION OF THE INVENTION

Figure 1A:
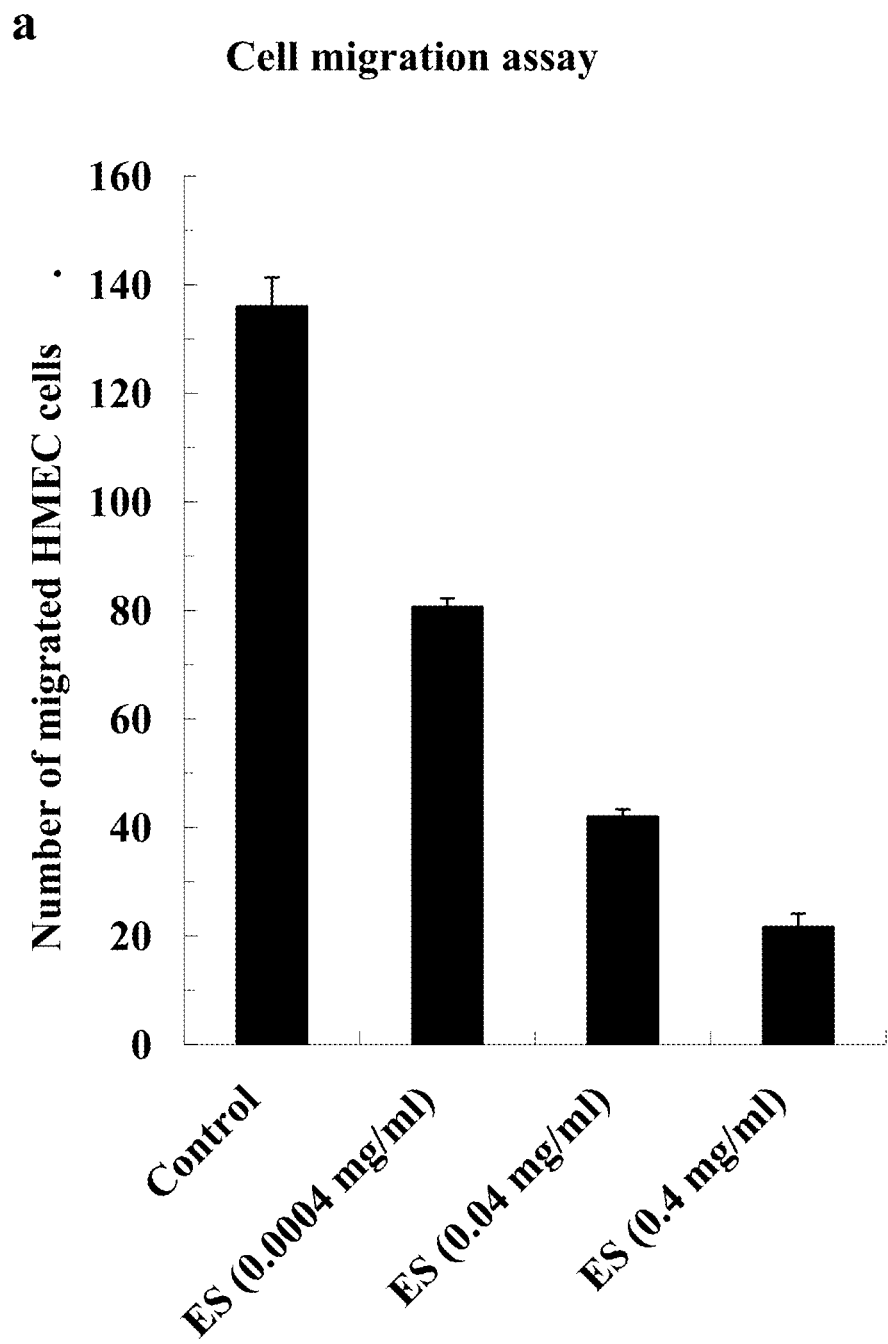
FIG. 1 shows that HMEC (human microvascular endothelial cells) is a sensitive cell line in response to ES in migration and proliferation. a, Cell migration assay were performed with HMECs in the presence of ES at concentrations as indicated, PBS serves as a control. b, Cell proliferation assay of HMECs was determined in the presence of ES at concentrations as indicated, and PBS serves as a control. The number of cells was evaluated by MTT assay. Results are means±s.e.m., n=3 (a), and n=5 (b).

The present invention derives partly from the discovery that nucleolin acts as a specific receptor for ES and facilitates its function in antiangiogenesis.

NL is a ubiquitous, nonhistone protein, which was first isolated from nucleolus. It is very interesting that the amount of NL is correlated to cell proliferation, which is regulated by Granzyme A and self-cleaving activity. Nucleolin also undergoes self-cleavage, which is decreased when cells enter a proliferative stage, as well as being cleaved by Granzyme A, an esterase secreted by cytotoxic lymphocytes (Chen et al., J. Biol. Chem., 1991, 266, 7754-7758; Fang and Yeh, Exp. Cell. Res., 1993, 208, 48-53; Pastemack et al., J. Biol. Chem., 1991, 266, 14703-14708). The cleavage and concomitant degradation of the protein provides for post-translational regulation of nucleolin.

As a multifunctional protein, NL exerts a critical and fundamental effect on cell proliferation, including organization of nucleolar chromatin, packaging of pre-RNA, rDNA transcription, and ribosome assembly. These activities are regulated by certain protein kinases such as casein kinase 2 (CK2) and cdc2 which are under strict control of other cell cycle proteins. Moreover, NL also functions as a cell surface receptor, shuttling between cell surface, cytoplasm, and nucleus. As a receptor of many viruses and cytokines, NL triggers the internalization of ligands as soon as these ligands bind to it.

Nucleolin has been described by Orrick et al (1973) as a protein with molecular weight about 100-110 kDa, and mainly existing in the nucleus of the propagating cells. Nucleolin exhibits auto-degradation and shows two degraded bands about 70 and 50 kDa in Western blotting analysis. Nucleolin is highly phosphorylated and methylated, and can be ADP-ribosylated. Because synthesis of the nucleolin is positively correlated with increased rate of cell division, tumor cells and rapidly dividing cells have higher levels of nucleolin content. The sequence of NL was reported earlier in Srivastava, et al., Cloning and sequencing of the human nucleolin cDNA. FEBS Lett. 250 (1), 99-105 (1989)

Nucleolin (also known as P92 and C23) is the most abundant nucleolar phosphoprotein in actively growing cells (Srivastava et al., FEBS Lett., 1989, 250, 99-105; Srivastava et al., J. Biol. Chem., 1990, 265, 14922-14931). It has been described by several groups and shown to participate primarily in ribosome biogenesis (Ghisolfi et al., Mol. Biol. Rep., 1990, 14, 113-114; Sipos and Olson, Biochem. Biophys. Res. Commun., 1991, 177, 673-678) and transport of ribosomal components (Schmidt-Zachmann et al., Cell, 1993, 74, 493-504). Nucleolin contributes to ribosome biosynthesis by transiently binding to the pre-ribosomes in the nucleolus via a ribonucleoprotein consensus sequence (Bugler et al., J. Biol. Chem., 1987, 262, 10922-10925; Ghisolfi-Nieto et al., J. Mol. Biol., 1996, 260, 34-53; Sapp et al., Eur. J. Biochem., 1989, 179, 541-548). Here, nucleolin can represent up to 5% of the total nucleolar protein (Lapeyre et al., Proc. Natl. Acad. Sci. U.S.A., 1987, 84, 1472-1476; Sapp et al., Eur. J. Biochem., 1989, 179, 541-548). However, it has also been shown to be involved in cytokinesis, nucleogenesis, cell proliferation and growth, transcriptional repression, replication, signal transduction and chromatin decondensation reviewed in (Tuteja and Tuteja, Crit. Rev. Biochem. Mol. Biol., 1998, 33, 407-436).

The multifunctionality of this protein arises from the presence of distinct structural and functional domains within the protein (Creancier et al., Mol. Biol. Cell., 1993, 4, 1239-1250; Sapp et al., Eur. J. Biochem., 1989, 179, 541-548). Three domains have been described within the nucleolin protein, the N-terminal domain, the central domain and the C-terminal domain. Contained in the N-terminal domain are sequences that show homology with the high-mobility group (HMG) and are responsible for interactions with chromatin (Erard et al., Eur. J. Biochem., 1988, 175, 525-530). The central domain contains four RNA recognition motifs and binds specifically with the short stem loop of the 18S and 28S ribosomal RNA (Bugler et al., J. Biol. Chem., 1987, 262, 10922-10925) while the C-terminal domain contains regions that are capable of unstacking bases in RNA (Gbisolfi et al., Mol. Biol. Rep., 1990, 14, 113-114; Ghisolfi-Nieto et al., J. Mol. Biol., 1996, 260, 34-53). Nucleolin contains a bipartite nuclear localization signal, spanning both the N-terminal and central regions of the protein, which facilitates transport into the nucleus where nucleolin accumulates due to interactions with other proteins (Schmidt-Zachmann and Nigg, J. Cell Sci., 1993, 1005, 799-806).

The domain structure of nucleolin has led the protein to be classified as an Ag—NOR protein (Active ribosomal gene located in the Nucleolar Organizer Region) otherwise known as markers of active ribosomal genes (Roussel et al., Exp. Cell. Res., 1992, 203, 259-269). It has been shown that transcription of ribosomal genes requires the presence of Ag—NOR proteins and the expression of Ag—NOR proteins has been associated with the prediction of tumor growth rate in cancers.

Nucleolin has also been purified as a matrix attachment region (MAR) binding protein from human erythroleukemia cells. In these studies, nucleolin was shown to participate in the anchoring of chromatin loops to the nuclear matrix (Dickinson and Kohwi-Shigematsu, Mol. Cell. Biol., 1995, 15, 456-465).

Nucleolin is highly phosphorylated and has been shown to be a substrate for casein kinase II (Csermely et al., J. Biol. Chem., 1993, 268, 9747-9752; Schneider and Issinger, Biochem. Biophys. Res. Commun., 1988, 156, 1390-1397), Protein kinase C-.xi. (Zhou et al., J. Biol. Chem., 1997, 272, 31130-31137), and Cdc2 (Belenguer et al., Mol. Cell. Biol., 1990, 10, 3607-3618). Furthermore, the phosphorylation of nucleolin has been shown to regulate the subcellular localization of the protein.

Nucleolin also undergoes self-cleavage, which is decreased when cells enter a proliferative stage, as well as being cleaved by Granzyme A, an esterase secreted by cytotoxic lymphocytes (Chen et al., J. Biol. Chem., 1991, 266, 7754-7758; Fang and Yeh, Exp. Cell. Res., 1993, 208, 48-53; Pasternack et al., J. Biol. Chem., 1991, 266, 14703-14708). The cleavage and concomitant degradation of the protein provides for post-translational regulation of nucleolin.

Anti-nucleolin antibodies have been found in the sera of patients with systemic connective tissue diseases including systemic lupus erythromatosus (SLE) (Minota et al., J. Immunol., 1990, 144, 1263-1269; Minota et al., J. Immunol., 1991, 146, 2249-2252) and scleroderma-like chronic graft vs. host disease (Bell et al., Br. J. Dermatol., 1996, 134, 848-854). The pharmacological modulation of nucleolin expression may therefore be an appropriate point of therapeutic intervention in pathological conditions.

Currently, there are no known therapeutic agents which effectively inhibit the synthesis of nucleolin. Consequently, there remains a long felt need for agents capable of effectively inhibiting nucleolin function.

It is believed that expression level of nucleolin correlates with cell proliferation rate. Nucleolin levels are highest in tumors and moderate in other rapidly dividing cells. It can be used in studies of different cancer cell lines as useful marker for cell proliferation. Since nucleolin plays a vital role in tumor cell proliferation, the present invention provides a strategy of inhibition of nucleolin expression to suppress the growth rate of tumor cells.

Endostatin (referred to herein as "ES") is a 20 kDa C-terminal globular domain of the collagen-like protein, collagen XVIII. It was originally isolated from the supernatant of a cultured murine hemangioendothelioma cell line for its ability to inhibit the proliferation of capillary endothelial cells. In animal tests, tumor dormancy was induced following repeated cycles of ES treatment without any drug resistance. Moreover, low toxicity of ES was observed in both animal tests and clinical trials. ES exhibits potent activities in inhibiting endothelial cell proliferation, migration, adhesion, survival, and in inducing cell apoptosis. Although integrins, tropomyosin, glypicans, and E-selectin are speculated as ES receptors associated with cell migration, and β-catenin and Shb adaptor are involved in ES-induced endothelial cells G1 arrest and apoptosis, the exact molecular mechanism of ES in antiangiogenesis is still in debate, and the reason for the low toxicity of ES in animal tests and clinical trials is still unknown. In addition, there is still a lack of adequate explanation for the fact that high concentration of ES is required in order to achieve antitumor effect in both animal tests and clinical trials.

The novel discovery, as disclosed here in the present invention, that nucleolin is a specific receptor to which endostatin binds, and mediates endostatin's function as an angiogenesis inhibitor provides a basis to screen and generate additional small molecules which also can function as angiogenesis inhibitor, and yet possesses additional properties that are more readily adapted as compared to the protein endostatin.

It has been shown that in order for endostatin to function effectively as an angiogenesis inhibitor, a large quantity of endostatin must be produced and administered into the cancer subjects, such as a mammal or a human, in order to produce the desired anticancer effect. The production of endostatin can be prohibitively expensive due to the demand of high dose in cancer therapy using endostatin. Thus, there exists a great need to find alternative methods to find angiogenesis inhibitors other than endostatin, which can be used effectively and economically produced in reducing cancer growth.

In addition, in order to increase the sensitivity of tumor cells to endostatin, methods are disclosed in the present invention whereby exogenous NL is introduced into target cells so that the cells will express higher than normal amount of surface NL. These modified target cells are more sensitive to the action of ES molecules due to the presence of high level of NL molecules, which as described above, act as the specific receptor for ES.

In another aspect of the invention, antibodies against NL can be used to screen those cancer cells or endothelial cells which express a high level of surface NL. Finding this particular group of patients is extremely beneficial to the effectiveness of angiogenesis-related cancer therapy, since patients with high expression of surface NL are ideal for the administration of ES in order to inhibit their tumor growth.

As used herein, the term "endostatin" (also known as "ES") refers to a protein that is preferably 18 kDa to 21 kDa in size as determined by non-reduced and reduced gel electrophoresis, respectively. The term endostatin also includes precursor forms of the 18 kDa to 20 kDa protein. The term endostatin also includes fragments of the 18 kDa to 20 kDa protein and modified proteins and peptides that have a substantially similar amino acid sequence, and which are capable of inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "endostatin" includes shortened proteins or peptides wherein one or more amino acids is removed from either or both ends of endostatin, or from an internal region of the protein, yet the resulting molecule retains endothelial proliferation inhibiting activity. The term "endostatin" also includes lengthened proteins or peptides wherein one or more amino acid is added to either or both ends of endostatin, or to an internal location in the protein, yet the resulting molecule retains endothelial proliferation inhibiting activity. Such molecules, for example with tyrosine added in the first position are useful for labeling such as radioiodination with $^{125}$I iodine for use in assays. Labeling with other radioisotopes may be useful in providing a molecular tool for destroying the target cell containing endostatin receptors.

Similarly, as used herein, the term "nucleolin" (also known as "NL") refers to a protein that is preferably 100 kDa (The exact MW of 80 kDa without post-modification) in size as determined by reduced gel electrophoresis. The term nucleolin also includes precursor forms of the 100 kDa protein. The term nucleolin also includes fragments of 100 kDa protein and modified proteins and peptides that have a substantially similar amino acid sequence, and which are capable of inhibiting proliferation of endothelial cells. For example, silent substitutions of amino acids, wherein the replacement of an amino acid with a structurally or chemically similar amino acid does not significantly alter the structure, conformation or activity of the protein, is well known in the art. Such silent substitutions are intended to fall within the scope of the appended claims.

It will be appreciated that the term "nucleolin" includes shortened proteins or peptides wherein one or more amino acids is removed from either or both ends of nucleolin, or from an internal region of the protein, yet the resulting molecule retains its specific binding activity for ES. The term "nucleolin" also includes lengthened proteins or peptides wherein one or more amino acid is added to either or both ends of nucleolin, or to an internal location in the protein, yet the resulting molecule retains the specific ES related NL activity. Such molecules, for example with tyrosine added in the first position are useful for labeling such as radioiodination with 125 Iiodine for use in assays.

The term "NL-specific" refers to the ability of NL binding to an angiogenesis inhibitor, and mediates its inhibition activity.

The term "angiogenesis-dependent" refers to those cancers and tumors whose growth or migration require angiogenesis, including those that would require for their growth in either volume or mass, or both, an increase in the number and density of the blood vessels supplying them with blood.

As used herein, the term "subject" refers to any animal, such as a mammal, including but not limited to a human, a non-human primate, a rodent, a pig, a rabbit, and the like, which is to receive a particular treatment, or undergoing a particular procedure such as screening for the level of presence of a particular molecule.

As used herein, the term "sample" is used in its broadest sense, including, but not limited to a biological sample and environmental sample. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, minerals, crystals and industrial samples. Such examples are not to be construed as limiting the sample types encompassed by the present invention.

As used herein, the term "label" encompasses chemical or biological molecules that are used in detecting the presence in a sample of a target molecule which is capable of binding to or otherwise interact with the label so as to indicate its presence in the sample, and the amount of the target molecule in the sample. Examples of such labels include, but not limited to, a nucleic acid probe such as a DNA probe, or RNA probe, an antibody, a radioisotope, a fluorescent dye, and the like.

As used herein, the term "usage instruction" includes instructions in the kit for carrying out the procedure for detecting the presence of a target molecular such as nucleolin in the sample to be tested. In the context of kit being used in the United States, the usage instruction comprising the statement of intended use required by the U.S. Food and Drug Administration (FDA) in labeling in vitro diagnostic products. It would be apparent to one with ordinary skill in the art of medical diagnostic devices as to the format and content of these usage instructions as required by the FDA.

As used in the present invention, an appropriate binding assay for selecting specific NL-related angiogenesis inhibitor includes HPLC, immunoprecipitation, fluorescent-binding assay, capillary electrophoresis, and so forth.

As used herein, an "anti-angiogenesis assay" is an experiment where a pool of candidate molecules are screened in order to discover the effectiveness of the candidate molecules in inhibiting angiogenesis. In order to discover whether a molecule has anti-angiogenesis property, various methods can be applied to carry out the present invention. For example, proteins and peptides derived from these and other sources, including manual or automated protein synthesis, may be quickly and easily tested for endothelial proliferation inhibiting activity using a biological activity assay such as the bovine capillary endothelial cell proliferation assay. Other bioassays for inhibiting activity include the chick embryonic chorioallantoic membrane (CAM) assay, the mouse corneal assay, and the effect of administering isolated or synthesized proteins on implanted tumors. The chick CAM assay is described by O'Reilly, et al. in "Angiogenic Regulation of Metastatic Growth", Cell, vol. 79 (2), Oct. 21, 1994, pp. 315-328, which is hereby incorporated by reference in its entirety. Additional anti-angiogenesis assays for screening for angiogenesis inhibitors can be found in Yu, et al., PNAS, Vol. 101, No. 21, pp 8005-8010 (2004), which is hereby incorporated by reference in its entirety.

As used herein, the term "and/or" as used in the phrase "proliferation and/or migration" refers to two situations: 1) both proliferation and migration of endothelial cells are modulated; 2) either proliferation or migration, but not both, of endothelial cells are modulated.

As used herein, the term "link" refers to connecting antibody to a cytotoxic agent such as a cytokine molecule, using conventional, well-known biological or chemical techniques such as cross-linking, and so forth.

The NL molecules can be used to generate polyclonal or monoclonal antibodies, which can in turn be used to both identify and quantify the level of NL in a particular target cells. NL labeled with appropriate markers such as radio-isotopes and fluorescent dye can be used to for the detection of endostatin in body fluids and tissues for the purpose of diagnosis or prognosis of angiogenesis-mediated diseases such as cancer. The present invention also includes methods of treating or preventing angiogenic diseases and processes including, but not limited to, arthritis and tumors by increasing the efficacy of endostatin in those angiogenesis-dependent cancers in a patient.

In some embodiments of the invention, methods such as flow cytometry as well as Enzyme-linked Immunosorbent Assay (ELISA) techniques are used for quantification of the NL peptide.

Detection of the nucleic acid molecules of NL can be performed using standard molecular biological techniques such as DNA probe hybridization, PCR, etc. General references for methods that can be used to perform the various PCR and cloning procedures described herein can be found in Molecular Cloning: A Laboratory Manual (Sambrook et al., eds. Cold Spring Harbor Lab Publ. 1989, latest edition). Detection of the RNA molecules of NL can be performed using Northern blot analysis. Northern blot analysis involves the separation of RNA and hybridization of a complementary labeled probe. In certain embodiments, RNA (or corresponding cDNA) is detected by hybridization to an oligonucleotide probe. A variety of hybridization assays using a variety of technologies for hybridization and detection are available. For example, in some embodiments, the TaqMan assay (PE Biosystems, Foster City, Calif.; See e.g., U.S. Pat. Nos. 5,962,233 and 5,538,848, each of which is herein incorporated by reference) is utilized. The assay is performed during a PCR reaction. The TaqMan assay exploits the 5'-3' exonuclease activity of the AMPLITAQ GOLD DNA polymerase. A probe consisting of an oligonucleotide with a 5'-reporter dye (e.g., a fluorescent dye) and a 3'-quencher dye is included in the PCR reaction. During PCR, if the probe is bound to its target, the 5'-3' nucleolytic activity of the AMPLITAQ GOLD polymerase cleaves the probe between the reporter and the quencher dye. The separation of the reporter dye from the quencher dye results in an increase of fluorescence. The signal accumulates with each cycle of PCR and can be monitored with a fluorimeter.

In certain other embodiments, reverse-transcriptase PCR (RT-PCR) is used to detect the expression of RNA. In RT-PCR, RNA is enzymatically converted to complementary DNA or "cDNA" using a reverse transcriptase enzyme. The cDNA is then used as a template for a PCR reaction. PCR products can be detected by any suitable method, including but not limited to, gel electrophoresis and staining with a DNA specific stain or hybridization to a labeled probe. In some embodiments, the quantitative reverse transcriptase PCR with standardized mixtures of competitive templates method described in U.S. Pat. Nos. 5,639,606, 5,643,765, and 5,876,978 (each of which is herein incorporated by reference) is utilized.

Detection of the protein molecule of NL can be performed using techniques known in the art (e.g., radioimmunoassay, ELISA (enzyme-linked immunosorbant assay), "sandwich" immunoassays, immunoradiometric assays, gel diffusion precipitation reactions, immunodiffusion assays, in situ immunoassays (e.g., using colloidal gold, enzyme or radio-isotope labels, for example), Western blots, precipitation reactions, agglutination assays (e.g., gel agglutination assays, hemagglutination assays, etc.), complement fixation assays, immunofluorescence assays, protein A assays, and immunoelectrophoresis assays, etc.

For example, antibody binding is detected by detecting a label on the primary antibody. In another embodiment, the primary antibody is detected by detecting binding of a secondary antibody or reagent to the primary antibody. In a further embodiment, the secondary antibody is labeled. Many methods are known in the art for detecting binding in an immunoassay and are within the scope of the present invention.

In certain cases, an automated detection assay is utilized. Methods for the automation of immunoassays include those described in U.S. Pat. Nos. 5,885,530, 4,981,785, 6,159,750, and 5,358,691, each of which is herein incorporated by reference. In some embodiments, the analysis and presentation of results is also automated. For example, in some embodiments, software that generates a prognosis based on the presence or absence of a series of proteins corresponding to cancer markers is utilized.

Antibodies specific for NL and NL analogs-are made according to techniques and protocols well known in the art. The antibodies may be either polyclonal or monoclonal. The antibodies are utilized in well-known immunoassay formats, such as competitive and non-competitive immunoassays, including ELISA, sandwich immunoassays and radioimmunoassays (RIAs), to determine the presence or absence of the endothelial proliferation inhibitors of the present invention in body fluids. Examples of body fluids include but are not limited to blood, serum, peritoneal fluid, pleural fluid, cerebrospinal fluid, uterine fluid, saliva, and mucus.

The present invention provides isolated antibodies that can be used in the diagnostic kits in the detection of NL. In preferred embodiments, the present invention provides monoclonal antibodies that specifically bind to NL.

An antibody against NL in the present invention may be any monoclonal or polyclonal antibody, as long as it can recognize the protein. Antibodies can be produced by using NL or its analogue as the antigen using conventional antibody or antiserum preparation processes.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is. administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter with the antiserum and then measuring the activity of the labeling agent bound to the antibody. The cell fusion can be carried out according to known methods, for example, the method described by Koehler and Milstein (Nature 256:495 [1975]). As a fusion promoter, for example, Sendai virus (HVJ) or, preferably, polyethylene glycol (PEG), is used.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

The present invention provides for a method of inhibiting the proliferation and/or migration of endothelial cells by producing a combination antibody containing an anti-NL antibody linked to a cytotoxic agent such as a chemokine, i.e. a Tumor Necrosis Factor-alpha, etc. When such a combination antibody is administered to a cell sample including an endothelial cells, the anti-NL antibody will direct the toxic agent to the endothelial cells, and thus bring the toxic agent such as Tumor Necrosis Factor-alpha to act upon the endothelial cells, and killing the cell growth.

Methods of linking an antibody to a second agent such as a cytotoxic agent in order to form a combination antibody, also know as an immunotoxic, is well known in the art. Two major advances in the immunotoxin field have been the use of the recombinant DNA technique to produce recombinant toxins with better clinical properties and the production of single-chain immunotoxins by fusing the DNA elements encoding combining regions of antibodies, growth factors, or cytokines to a toxin gene.

First-generation immunotoxins were constructed by coupling toxins to MAb or antibody fragments using a heterobifunctional cross-linking agent. It was also discovered that genetic engineering could be used to replace the cell-binding domains of bacterial toxins with the Fv portions of antibodies or with growth factors.

As well known in the art, cylokines are small protein molecules that are the core of communication between immune system cells, and even between these cells and cells belonging to other tissue types. They are actively secreted by immune cells as well as other cell types. Cytokines that are produced by immune cells form a subset known as lymphokines. Their action is often local, but sometimes can have effects on the whole body.

There are a lot of known cytokines that have both stimulating and suppressing action on lymphocyte cells and immune response. Some of the better known cytokines include: histamine, prostaglandin, TNF-α, IL-1, and IL-6. There are three classes of cytokines.

The present invention provides kits for the detection and characterization of nucleolin in cancer diagnostics. In some embodiments, the kits contain antibodies specific for NL, in addition to detection reagents and buffers. In other embodiments, the kits contain reagents specific for the detection of mRNA or cDNA (e.g., oligonucleotide probes or primers) of NL. In preferred embodiments, the kits contain all of the components necessary to perform a detection assay, including all controls, directions for performing assays, and any necessary software for analysis and presentation of results.

Kits containing labels such as antibodies again NL for measurement of NL are also contemplated as part of the present invention. Antibody solution is prepared such that it can detect the presence of NL peptides in extracts of plasma, urine, tissues, and in cell culture media are further examined to establish easy to use kits for rapid, reliable, sensitive, and specific measurement and localization of endostatin. These assay kits include but are not limited to the following techniques; competitive and non-competitive assays, radioimmunoassay, bioluminescence and chemiluminescence assays, fluorometric assays, sandwich assays, immunoradiometric assays, dot blots, enzyme linked assays including ELISA, microtiter plates, antibody coated strips or dipsticks for rapid monitoring of urine or blood, and immunocytochemistry. For each kit the range, sensitivity, precision, reliability, specificity and reproducibility of the assay are established according to industry practices that are commonly known to and used by one with ordinary skill in the art.

Similarly, a diagnostic kit in the present invention can be used for localization of endostatin in tissues and cells. This NL immunohistochemistry kit provides instructions, NL molecules, preferably labeled and linked to a fluorescent molecule such as fluorescein isothiocyanate, or to some other reagent used to visualize the primary antiserum. Immunohistochemistry techniques are well known to those skilled in the art. This NL immunohistochemistry kit permits localization of endostatin in tissue sections and cultured cells using both light and electron microscopy. It is used for both research and clinical purposes. For example, tumors are biopsied or collected and tissue sections cut with a microtome to examine sites of endostatin production. Such information is useful for diagnostic and possibly therapeutic purposes in the detection and treatment of cancer.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example One

Nucleolin is an Endostatin-Binding Protein

To investigate the mechanism of action of ES, we isolated ES-binding proteins directly from the membrane proteins of human microvascular endothelial cells (HMECs) with immobilized ES. Nucleolin was identified as a critical member in the ES signaling network, and is the most interesting one in the network. Here we describe that NL serves as a novel receptor for ES, and mediates the activity of ES in antiangiogenesis.

Methodology:

Methods that are used in the study of NL and ES interactions are generally known in the art. Descriptions of these methods are provided as follows:

Cell Migration Assay

Endothelial cells (HMECs or HUVECs, $2 \times 10^4$ per well) were seeded into the upper chamber of Transwell™ filter (8 μm pores, Costar) with DMEM medium containing 0.5% FCS and 10 ng/ml VEGF (PeproTech EC). ES (from Protgen) with indicated concentrations and other reagents (NL and Anti-NL) were added in both upper chamber and lower chamber at the beginning of the migration assay. The endothelia cells were allowed to migrate for 6 h at 37° C. and 5% $CO_2$. After fixed with ethanol and stained with Eosin, the cells migrated completely through the filter to the lower chamber were calculated as the average number of cells observed in five random high-power (×400) fields per well in triplicate wells.

Cell Proliferation Assay

Endothelia cells (HMECs or HUVECs, $1 \times 10^3$ per well) were seeded in a 96-well plate with DMEM medium containing 0.5% FCS and 10 ng/ml bFGF. ES with indicated concentrations and other reagents were added at the beginning of the proliferation assay with a final volume of 200 μl per well. The endothelial cells were allowed to proliferate for 48 h at 37° C. and 5% $CO_2$. After 48 h incubation, the medium was replaced with DMEM medium without phenol red and 0.5 mg/ml MTT with a final volume of 100 μl. The cells were incubated further for 4 h at 37° C. and 5% $CO_2$. Subsequently, the cells were lysed with iso-propanol containing 0.05 M hydrochloride, and the absorbance at 570 nm was measured.

Identification of Isolated Proteins with MALDI-TOF Mass Spectrometry

Fractions obtained from the ES-Ni-NTA affinity column were applied to 12% SDS-PAGE, and the major bands were digested using sequencing grade porcine-modified trypsin (Promega). The peptides produced were analyzed by MALDI-TOF mass spectrometry using a Bruker Biflex linear time-of-flight spectrometer (Bruker Franzen), equipped with a multiprobe SCOUT source, ultra-nitrogen laser (337 nm), and a dual microchannel-plate detector. The MALDI-TOF data was searched against Swiss-Prot protein database for protein identification.

Indirect Immunofluorescence

The HMECs were incubated with ES (20 μg/ml) for 1 h at 37° C. and 5% $CO_2$. Without permeabilized, the HMECs were stained with indicated antibodies. FITC-linked goat anti-mouse IgG and TRITC-linked goat anti-rabbit IgG were used as the secondary antibodies. Confocal fluorescence imaging was performed on an Olympus Fluoview laser scanning confocal imaging system (Olympus Inc.). Images were captured using multiple photomultiplier tubes regulated by Fluoview 2.0 software (Olympus).

Production of Recombinant Nucleolin

The cDNA of NL was obtained from HMECs by RNA isolation and reverse transcription system (Promega). The sequence of NL fusing with a polyhistidine $(His)_6$ tag was subcloned into pPIC9K (Invitrogen). This plasmid was linearized with restriction enzyme Sal I (Promega) and electrotransformed into pichia strain GS115. A stable transformant was selected using G418 (Invitrogen) and then grown in a 30° C. shaking flask for 3 days in BMMY medium as described by the manufacturer. The supernatant was obtained and NL was purified with Ni-NTA nickel ion-affinity columns (Qiagen).

Preparation of Polyclonal Antibodies Against Nucleolin

New Zealand White rabbits were immunized with 50 μg of recombinant NL prepared by pPIC9K-GS115 pichia expression system as described previously. The initial subcutaneous injection was administered in Freund's complete adjuvant, and a booster dose of 50 μg was given intramuscularly on day 14 in Freund's incomplete adjuvant. Boosts of 50 μg of NL were given subcutaneously without any adjuvant at 4, 10, 16, and 22 weeks. At 1 week after the last boost, serum was obtained, and the IgG was purified by affinity chromatography on a protein A column (Amersham Biosciences), eluted with glycine-HCl buffer (0.15 M, pH 2.5), and immediately neutralized with 0.15 M Tris to a pH of 6.8-7.2. The combined fractions were filter-sterilized (0.2 μM), and aliquots of the antibodies preparation were stored at −80° C.

Cell Adhesion Assay

Cells to be tested were serum-starved for 30 min, and then seeded in a 96-well plate which is coated with endostatin (20 μg/ml) and polylysine (50 μg/ml). The plate was incubated for 1 h at 37° C. and 5% $CO_2$. Unbounded cells were removed by washing with fresh medium gently. The remained cells were stained with crystal violet (0.1% in $ddH_2O$) for 25 min at RT. The plated was washed with tape water, and the remained crystal violet was solubilized with 0.5% Triton X-100 (diluted in $ddH_2O$). The absorbance at 570 nm was measured.

Figure 1B:
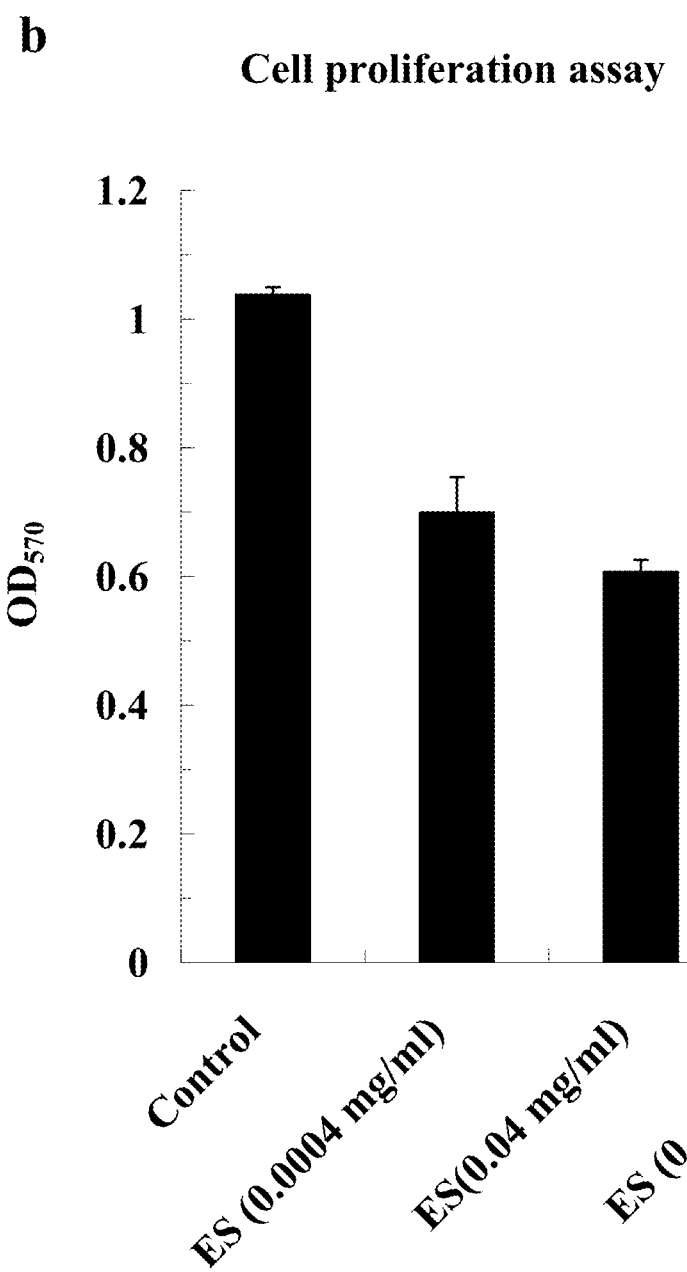

As the targets of many angiogenesis inhibitors, endothelial cells are used as models for antiangiogenesis assays in vitro. Unfortunately, the results are usually variable and inconsistent, probably due to the fact that the assays are not well established and the cell lines are not so stable. To this end, HMEC cell line was chosen that meets the criteria as a good model for antiangiogenesis assay. In the cell migration assay, ES inhibited the migration of HMECs stimulated by VEGF in a dose dependent manner and the half-maximal inhibitory concentration (IC50) was observed at 4 μg/ml (FIG. 1a). ES inhibited the migration of HMECs by 15% even at a concentration as low as 4 μg/ml (data not shown). Similar results were also obtained in the proliferation assay of HMECs with bFGF as a stimulus (FIG. 1b). The results from both the cell migration assay and the proliferation assay demonstrate that HMECs are very sensitive to ES such that reliable and consistent results can be obtained.

Figure 2A:
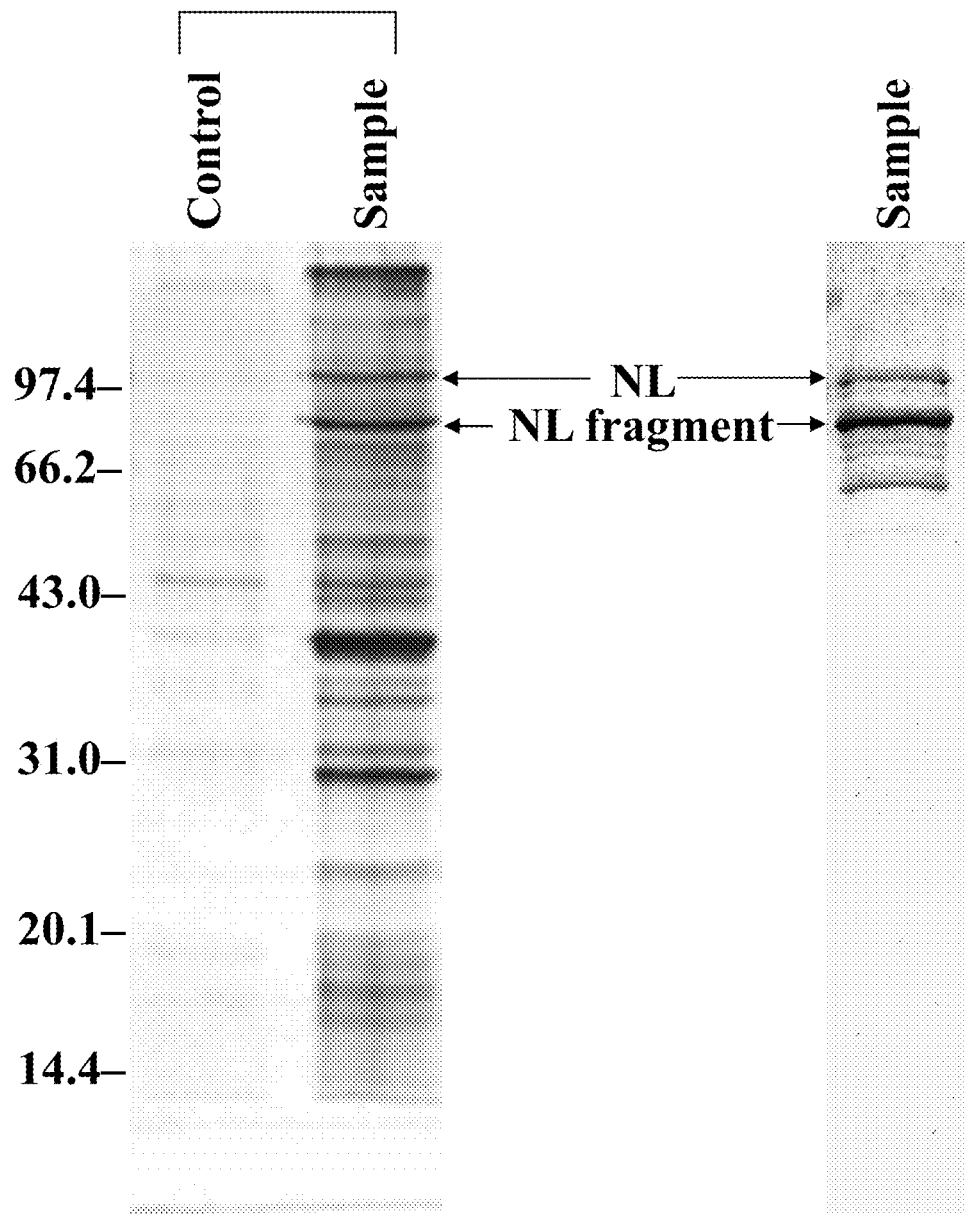
FIG. 2 shows that ES binds to cell surface NL. a, ES binding proteins isolated from the cell surface of HMECs were identified as NL and its fragment. The ES binding proteins were isolated from HMECs' plasma membrane using ES-Ni-NTA affinity beads as described in methods. The fractions eluted with 500 mM sodium chloride in PBS buffer were applied to SDS-PAGE (left panel) and immunoblotting using monoclonal antibodies against NL (right panel). b, ES binds NL specifically in vitro. Immunoprecipitation was carried out using recombinant NL and ES. c, Heparin interrupts the formation of ES-NL complex. Immunoprecipitation using recombinant NL and ES was carried out in vitro with or without heparin (200 nM). d, ES binds HMECs specifically via its surface NL. HMECs were incubated with ES and different concentrations of antibodies against NL for 30 min at RT, and then were washed for 3 times with PBS buffer. The cells were applied to SDS-PAGE and immunoblotting using antibodies against ES. β-actin was used as control. e, HMECs were incubated with ES (20 µg/ml) for different periods of time at 37° C. and 5% $CO_2$. After washed with fresh medium, immunoprecipitation and immunoblotting was carried out with antibodies against NL and ES, respectively. β-actin was used as control. f-i, co-localization of NL and ES on the surface of HMEC cells. Intact HEMC cells were stained with both mouse anti-NL antibody, and rabbit anti-ES antibody. Examination was conducted by indirect immunofluorescence using laser scanning confocal microscopy. Scale bar, 20 µm.
Figure 2B:
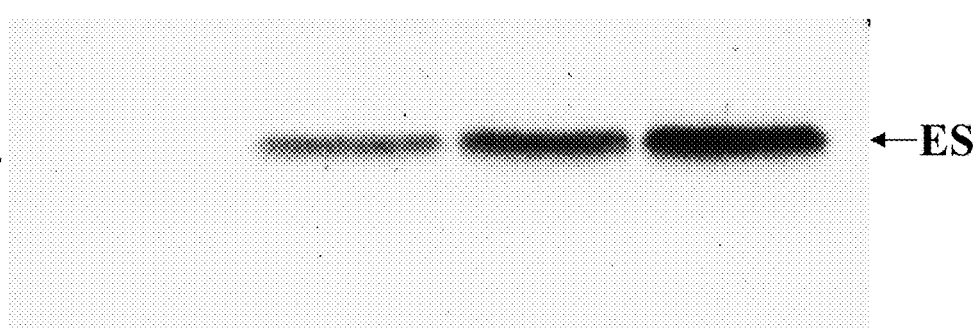
Figure 2C:
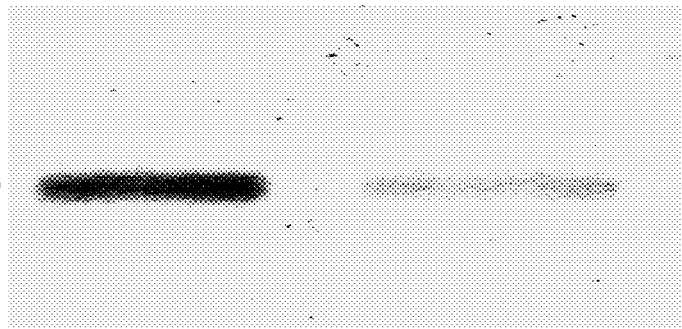
Figure 2D:
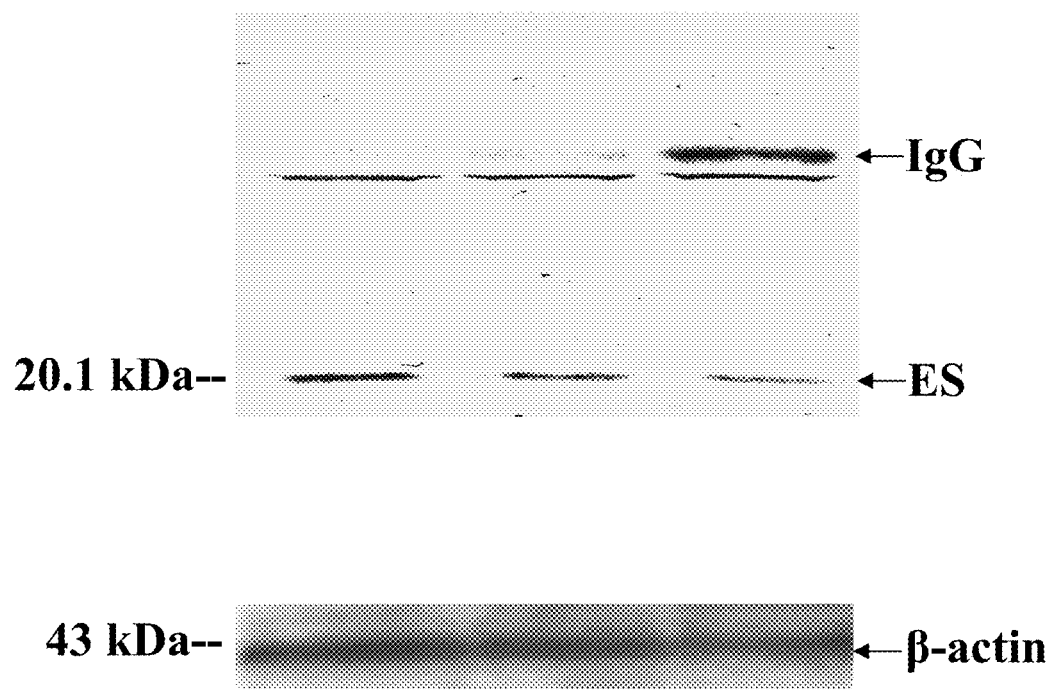

The sensitive response of HMECs to ES implies that HMECs may contain potential receptor(s) for ES. Moreover, ES can specifically bind HMECs under physiological conditions (see FIG. 2d below). We thus started to isolate ES receptor(s) from HMECs. Recombinant ES was pre-loaded on to Ni-NTA beads via its N-terminal His-tag. Crude fraction of plasma membrane of HMECs was prepared and treated with 1% Triton X-100 to release proteins from plasma membrane as described by Marshak et al. The prepared plasma membrane proteins were applied to the ES-Ni-NTA beads. Unbound proteins were removed from ES-Ni-NTA beads with PBS buffer. Every fraction was collected and subjected to analysis by reducing SDS-PAGE. The control was carried out in parallel, and the only difference was substituting Ni-NTA for ES-Ni-NTA. Two proteins with apparent molecular weights of 110 kDa and 80 kDa showed specific binding ability to ES-Ni-NTA beads (FIG. 2a), and were subsequently identified as NL (110 kDa) and its degraded fragment (80 kDa) by peptide mass fingerprinting using matrix-assisted laser desorption/ionization-time of flight-mass spectrometry (MALDI-TOF). The identity of NL was further verified by immunoblotting (IB) with monoclonal antibody against NL (FIG. 2a). To verify the interaction between ES and NL, the following studies were carried out. The results of immunoprecipitation (IP) in vitro show that the interaction between ES and recombinant NL is specific (FIG. 2b), and a complex is formed between ES and NL. This complex can be disrupted by 200 mM heparin (FIG. 2c). ES can also bind HMECs via NL because polyclonal antibodies against NL can block such binding (FIG. 2d). This conclusion was further verified by IP, which was carried out with ES-preincubated HMECs (FIG. 2e). The results show that ES and total endogenous NL (cell surface, cytoplasma, and nucleus) form a complex in living cells. Moreover, co-localization between ES and NL on cell surface of HMECs was also observed by laser scanning confocal immunofluorescence microscopy (FIG. 2f-i). Taken together, ES specifically binds to NL both in vitro and in vivo, which indicates that NL is a potential receptor for ES.

Example Two

Nucleolin is a Novel Receptor for Endostatin

Figure 3A:
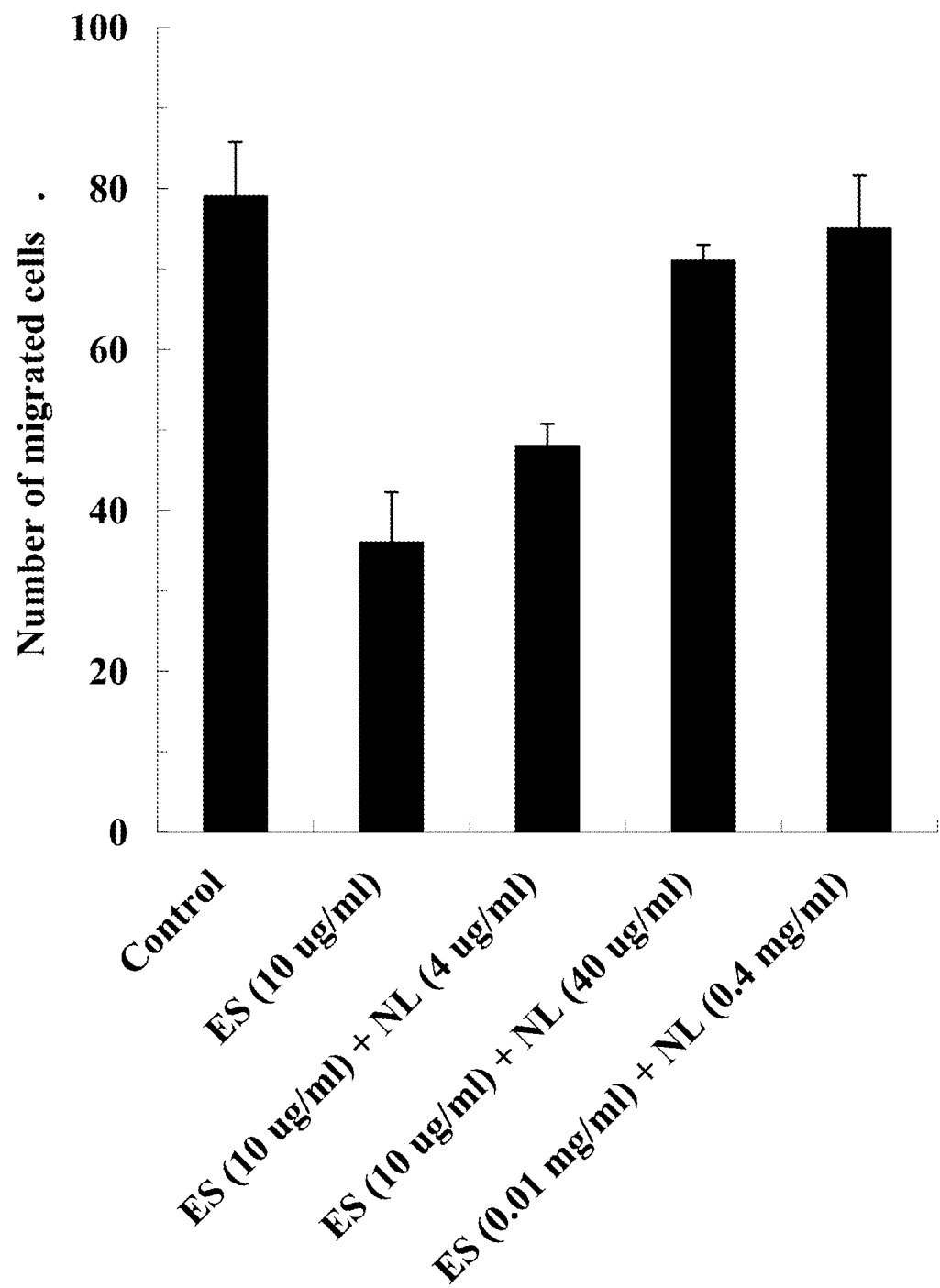
FIG. 3 shows that nucleolin is a receptor for endostatin. a, Indicated concentrations of recombinant NL were tested to lift the inhibition of ES in HUVECs migration assay, PBS serves as a control. b, Recombinant NL itself has no effect on cell migration. HUVECs migration assay was performed with indicated concentrations of ES, NL, and both of them, respectively, PBS is a control. c, HUVECs proliferation assay was performed with indicated concentrations of ES, NL, and Anti-NL, PBS as a control. The cell number was evaluated by MTT assay. d, Cell adhesion assay was performed with NL-deficient and control HMECs. NL-deficient cells were obtained by suppressing the expression of NL with RNAi plasmid BS/U6/1356. Control cells were transfected with blank plasmid BS/U6. Results are means±s.e.m., n=4 (a, d), n=5 (b, c). e, The suppression of expression of NL by RNAi plasmids was demonstrated by IB using Anti-NL. Plasmid BS/U6/1356 can suppress the expression of NL, but BS/U6/263 dose not work. The myosin blots serve as loading controls. f, Cell proliferation assay was performed with NL-deficient and control HMECs. NL-deficient cells were obtained by suppressing the expression of NL with RNAi plasmid BS/U6/1356. Control cells were transfected with blank plasmid pBS/U6. ES was added with indicated concentrations. The number of cells was evaluated by MTT assay.
Figure 3B:
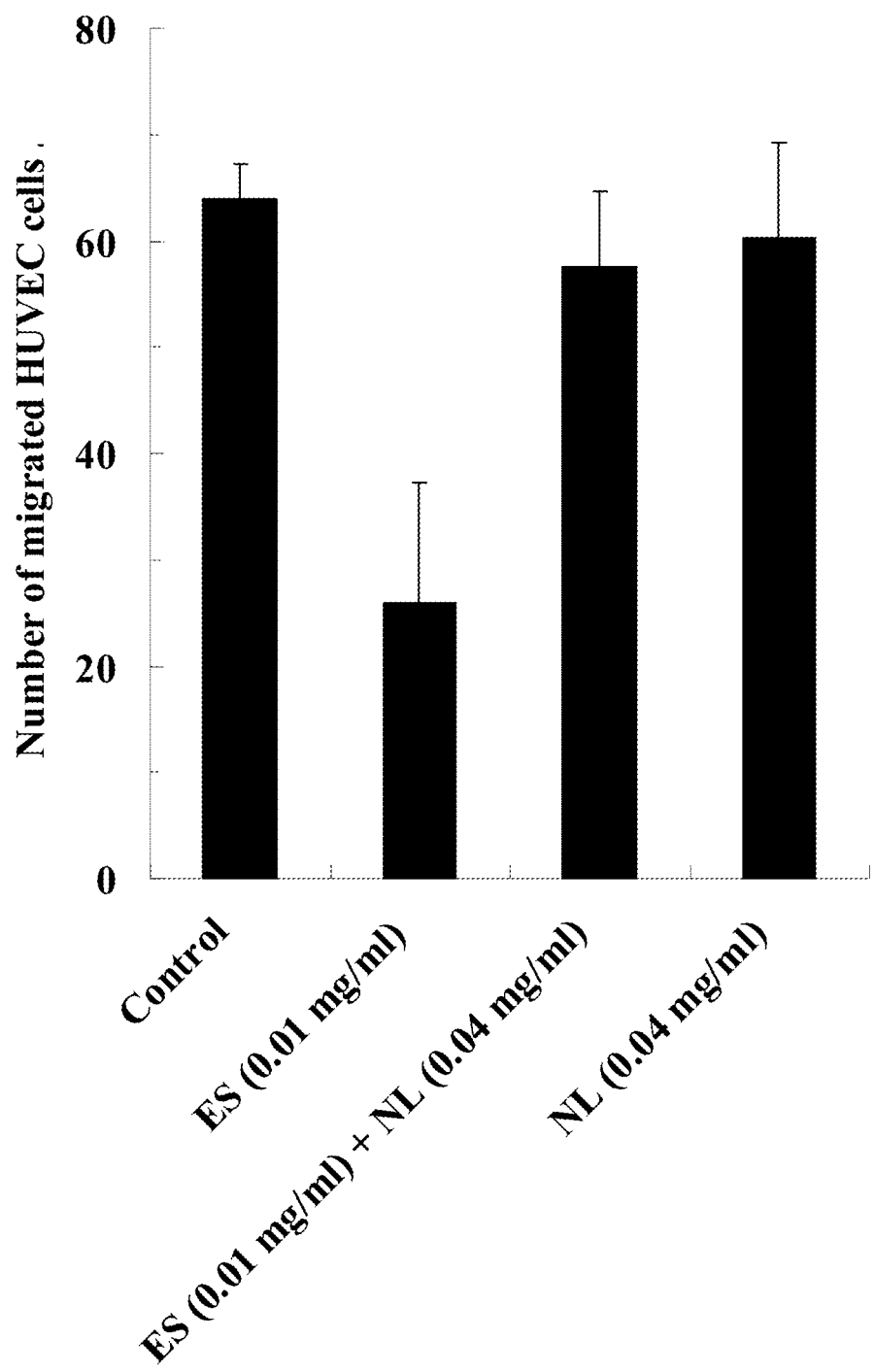
Figure 3C:
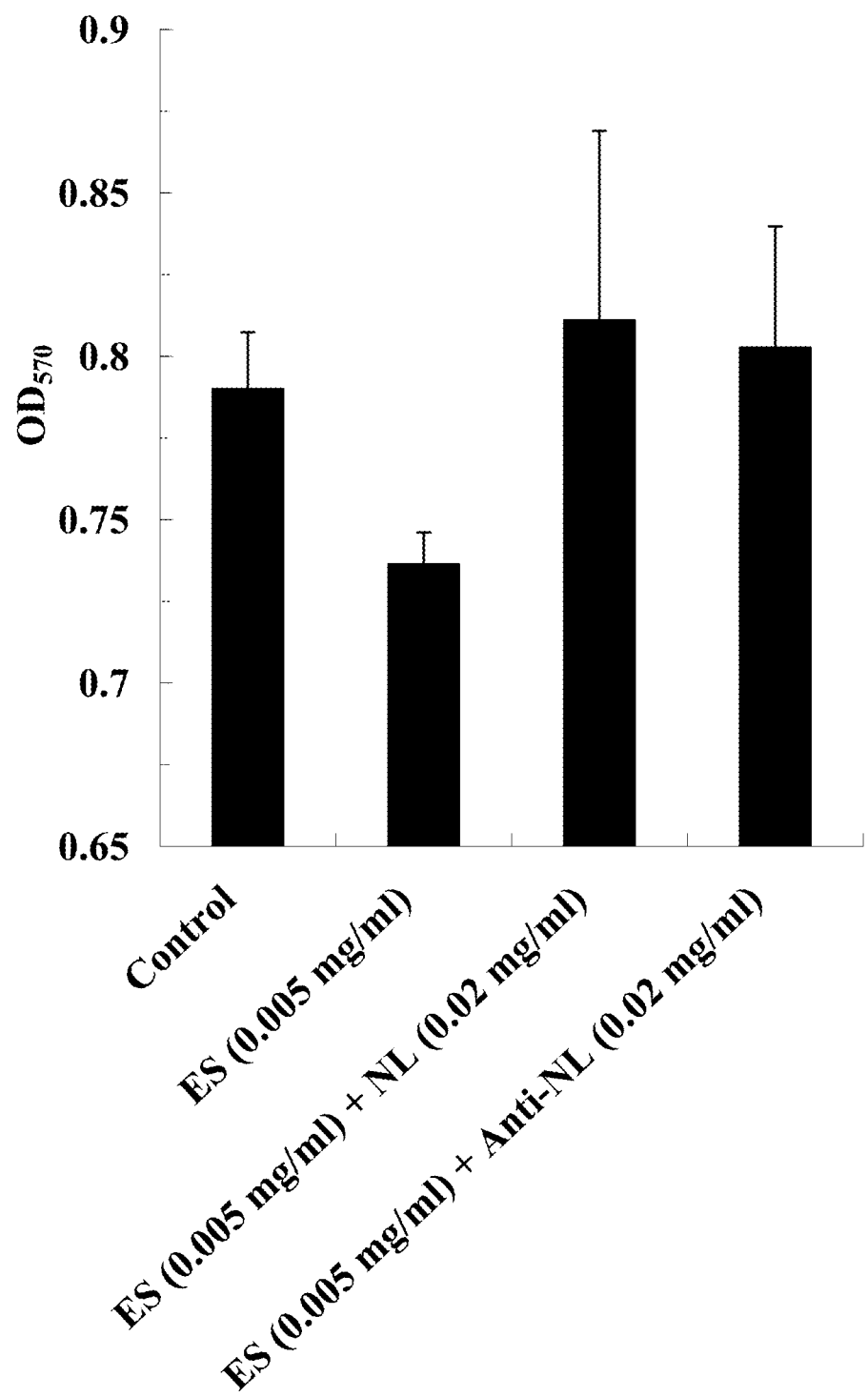
Figure 3D:
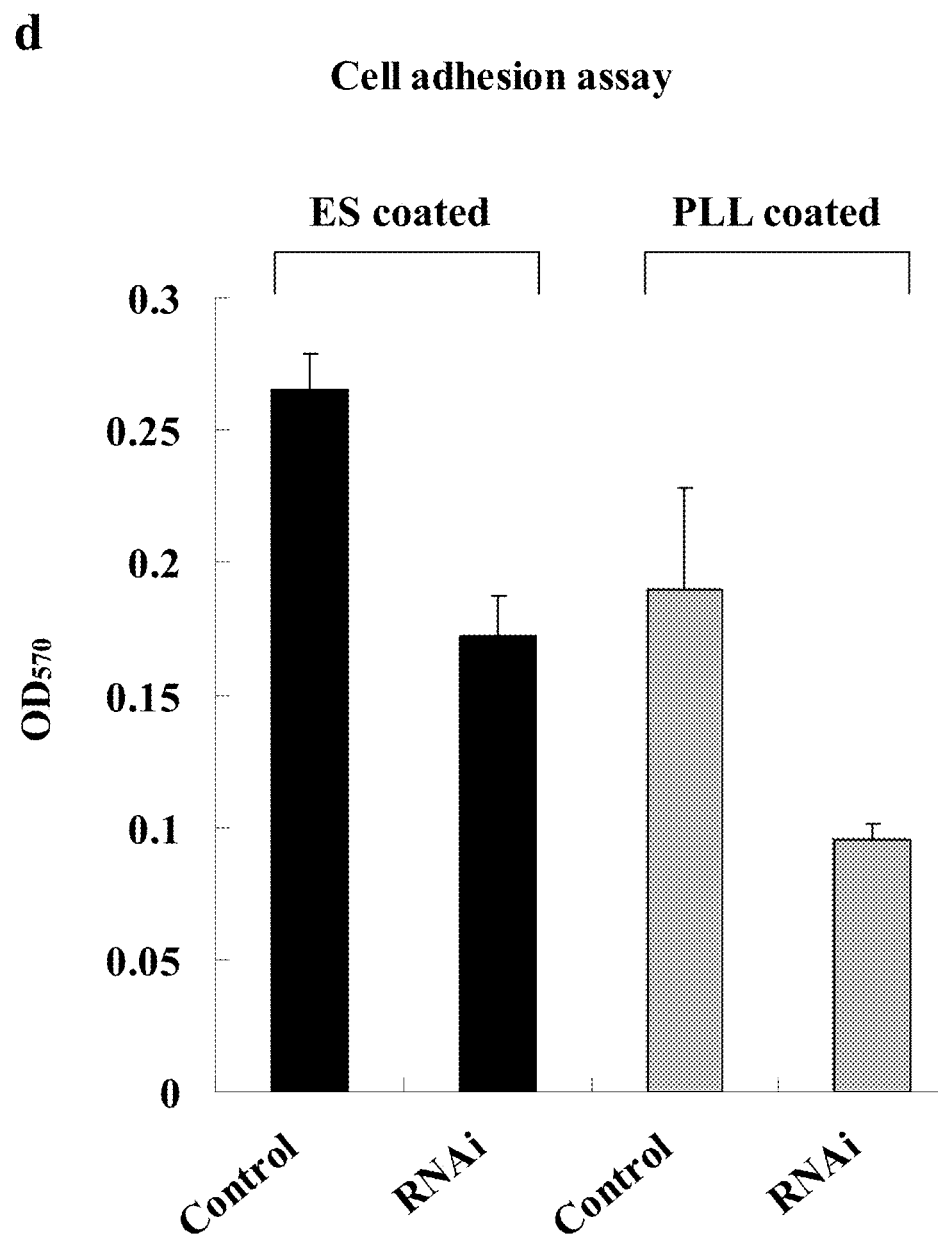
Figure 3E:
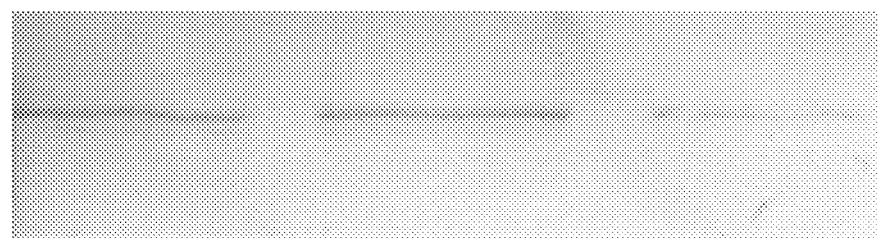
Figure 3E:
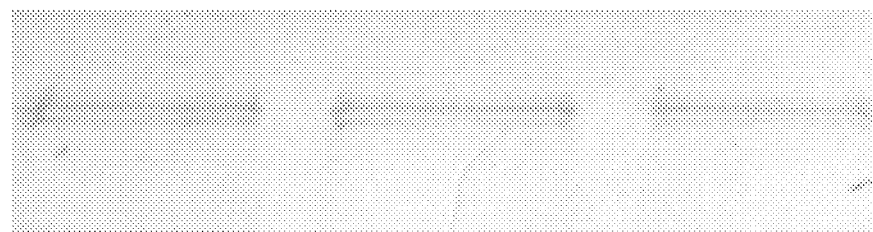
Figure 3F:
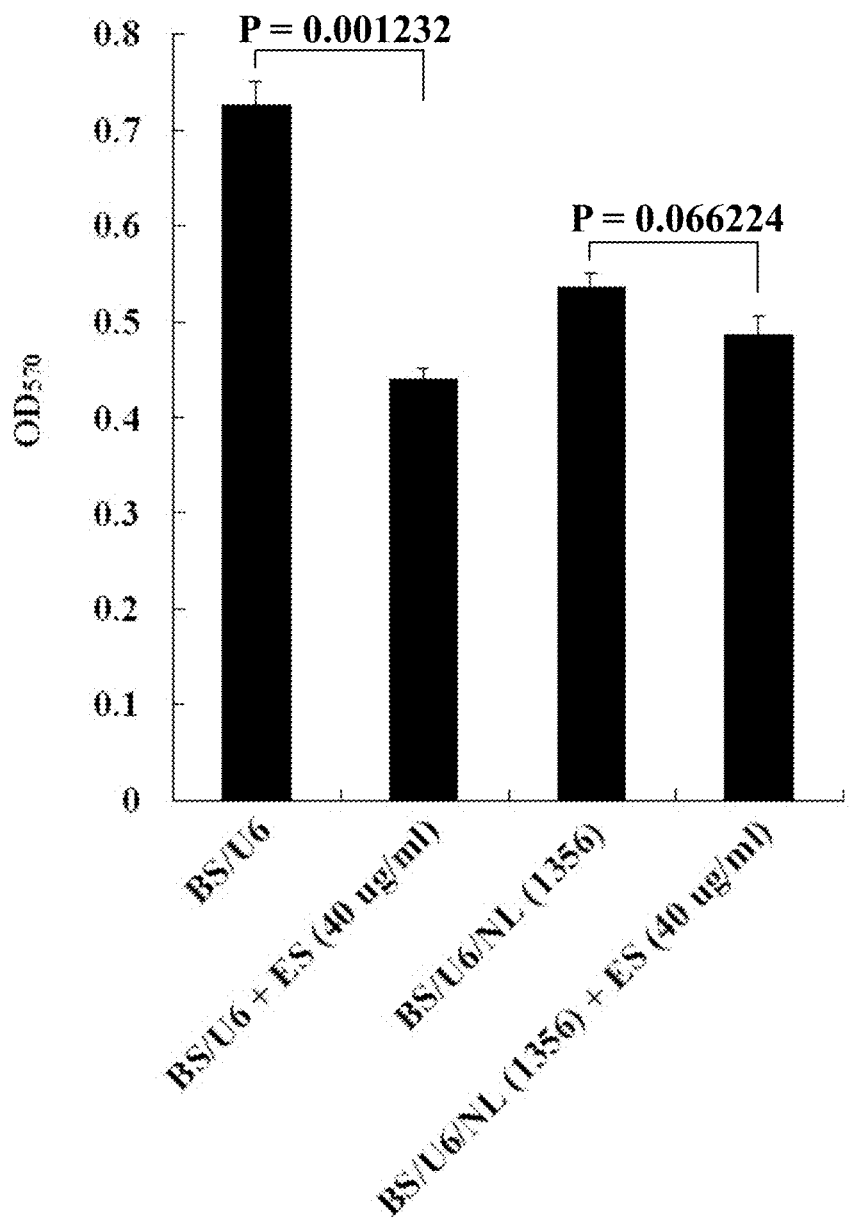

If NL is a receptor for ES, it should mediate the activities of ES in antiangiogenesis such as inhibiting the migration, proliferation, and adhesion of endothelial cells. To characterize the role of NL during the process of mediating ES activities, competitive cell migration and proliferation assays were therefore performed with ES, recombinant NL, and polyclonal antibodies against NL, respectively. Since NL was isolated from HMECs as a potential receptor for ES in antiangiogenesis, whether or not NL plays similar roles in other widely accepted endothelial cells should be demonstrated. To this end, human umbilical vein endothelial cell (HUVEC), isolated directly from umbilical veins, were subjected to competitive cell migration and proliferation assays. This kind of endothelial cells can migrate through a microporous (8 μm) membrane under stimulation of VEGF, and ES inhibits such migration. Recombinant NL lifted the inhibition of ES in the cell migration assay in a dose dependent manner (FIG. 3a), indicating that recombinant NL is involved in the antiangiogenesis activities of ES. The possibility that NL itself has a stimulating activity on the migration of endothelial cells was excluded because recombinant NL itself had no effect on cell migration as shown in FIG. 3b. Similar results were also obtained when the cell proliferation assay was performed with HUVECs (FIG. 3c). Not surprisingly, polyclonal antibodies against NL blocked the inhibition of ES on cell proliferation (FIG. 3c). In addition, as shown in FIG. 3f, where cell proliferation assay was performed with NL-deficient cells and control HMECs, it can be seen that the anti-angiogenesis effect of ES required the presence of NL molecule in the target cells. All these studies strongly suggest that NL is a receptor for ES in antiangiogenesis.

To further confirm that NL is the receptor for ES, the expression of NL was suppressed by RNA interference (RNAi), followed by evaluating such a change on cell adhesion, another important activity of ES in antiangiogenesis. The results show that adhesions of HMECs on both immobilized ES and immobilized polylysine, a synthetic extracellular matrix, significantly decreased when the expression of NL was suppressed by DNA vector-based RNAi (FIG. 3d), even though the expression of NL was not suppressed completely (FIG. 3e). Rehn et al. reported that the adhesion of endothelial cells on immobilized ES is critical for the activities of ES such as formation of focal adhesions and phosphorylation of FAK, and loss of this adhesion implies loss of functions of ES on endothelial cells. Along the lines of these studies, our results demonstrate that NL is essential for the activities of ES and the adhesion of endothelial cells to extracellular matrix (ECM). In sum, we conclude that NL is a novel receptor for ES and plays a key role in the signal transduction pathways of ES.

Example Three

Nucleolin Mediates Endostatin Signal Pathway

To unravel the exact role of NL in the signal transduction pathways of ES, we then investigated the down stream events. Retrospect that the amount of ES-NL complex varied when incubating ES with HMECs, and reached the maximal level around 2 h (FIG. 2e). ES may be internalized by HMECs via cell surface NL, and some of the internalized ES is degraded by HMECs subsequently. It seems that there is a balance between ES internalization and degradation (FIG. 2e).

To confirm that the internalization of ES is via cell surface NL, immunofluorescence localization was carried out with biotinylated ES. HMECs were incubated with biotinylated ES for different periods of time, and the process of internalization of ES was observed under fluorescence microscope after biotinylated ES was stained with TRITC-labeled streptavidin (FIG. 4a-f). Upon 30 min of incubation, most of the internalized ES distributed in cytoplasm but the amount was small (FIG. 4b). Upon 1 h of incubation, the internalized ES increased and began to accumulate in nuclei (FIG. 4c). The amount of internalized ES reached the maximum at about 2 h of incubation (FIG. 4d). By 3 h, the nucleus-accumulated ES began to disappear (FIG. 4e). By 7 h, little ES could be found in nuclei (FIG. 4f). There was a lag phase in the fluorescence assay (FIG. 4b-d) comparing with IP (FIG. 2e) for the amount of internalized ES to reach their maximals, probably the degradation rate of ES is faster than that of biotinylated ES. Importantly, the amount of internalized biotinylated ES was significantly reduced when HMECs were preincubated with polyclonal antibodies against NL, demonstrating that ES is internalized via cell surface NL (FIGS. 4d, g). Moreover, some small light dots inside the cells were observed under fluorescence microscope (FIG. 4b-e), which may suggest that ES is internalized in vesicles in the process of internalization. This observation is consistent with previous reports by Wickstrom and Christian et al.

To explain how NL mediates the internalization of ES, cross-linking experiments and IP were carried, respectively, during the process of internalization of ES. At first, we expected to isolate the complex of ES, NL, and other proteins in living HMECs with cross-linking reagents. A huge complex with a molecular weight far more than 300 kDa was thus obtained using BS3 (a cross-linking reagent from PIERCE Ltd.) (data not shown). Although this complex can be stained by antibodies against either ES or NL, none of the components could be identified by this method. Alternatively, IP with polyclonal antibodies against NL was introduced into lysed HMECs to isolate the proteins which interact directly with NL. A protein with a molecular weight around 200 kDa was thus found, and it was identified as non-muscle myosin by PMF using MALDI-TOF. Myosins constitute a huge superfamily, which is involved in membrane dynamics and actin organization at cell cortex, thus affecting cell migration, adhesion, and endocytosis. Within this superfamily, two-head class-V myosins can serve as transporters for vesicles, organelles, and mRNA particles along actin filaments. We also found that cell surface NL can bind ES and transport ES into cell nuclei (FIG. 4a-f). Since myosin is an intracellular protein, it must bind to the intracellular domain of cell surface NL. We speculate that this NL-myosin complex may serve as a transporter during the process of ES internalization. Similar process was also reported by Shibata et al. that midkine, a growth factor in neural cells, can also be internalized and located into nuclei via NL. Interestingly, antibodies against the N-terminus of NL can be internalized by Hep-2 cells via cell surface NL. Therefore, internalization appears to be a general phenomenon and is inevitable when a ligand binds to cell surface NL. The difference is that ES can inhibit cell proliferation whereas antibodies against NL cannot (FIG. 3c).

These observations indicate that although many ligands can bind to cell surface NL specifically and trigger their internalizations, their fates after internalization are different.

Figure 4H:
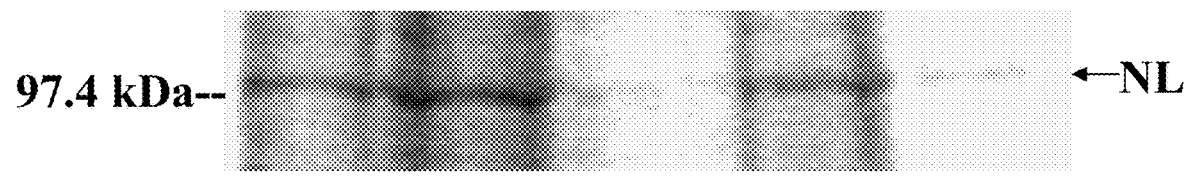
FIG. 4 shows that nucleolin mediates endostatin signal network. a-f, ES is internalized by HMECs. HMECs were incubated with or without (a) 10 µg/ml biotinylated ES for 0.5 h (b), 1 h (c), 2 h (d), 3 h (e), and 7 h (f), respectively. The internalized ES was stained with TRITC-labeled avidin. g, The internalized ES was blocked by incubating cell with Anti-NL. Scale bar, 25 µm. h, In nuclei, ES inhibits CK2-mediated NL phosphorylation. Phosphorylation assay was performed as described in Methods. Phosphorylated NL was detected by SDS-PAGE and autoradiography. The NL blots serve as loading controls. i-k, Colocalization of cell surface NL with integrin β1 on HMEC surface. Intact HMECs were stained by mouse Anti-NL and rabbit Anti-integrin β1, and detected by indirect immunofluorescence using laser scanning confocal microscopy. Scale bar, 10 µm.
Figure 4H:
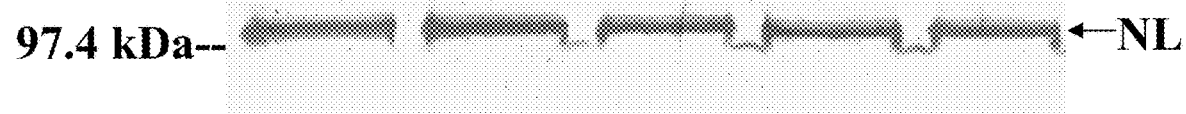

The functions of ES were then investigated when it was transported to nuclei. Bouche et al. reported that NL can promote rDNA transcription and ribosome biogenesis in nuclei, which are critical for cell survival and proliferation, as long as its serine residues in the N-terminus is phosphorylated by some kinds of kinases such as casein kinase 2 (CK2) under the stimulation of bFGF. Folkman and his colleagues also reported that proliferation of endothelial cells, which is stimulated by bFGF, could be inhibited by ES. According to the studies of Bouche et al., the bFGF-stimulated phosphorylation of NL is mediated by CK2 but not by any other kinases such as cdc2 in this isolated-nuclei system. Therefore, we speculate that ES inhibits cell proliferation by inhibiting the CK2-mediated phosphorylation of NL, which is stimulated by bFGF. To confirm this hypothesis, nuclei from quiescent HMECs were isolated and the phosphorylation assay was carried out with or without ES. The results show that phosphorylation of NL was inhibited when the nuclei of HMECs were preincubated with ES (FIG. 4h). Moreover, phosphorylation of NL is stimulated by bFGF rather than VEGF (FIG. 4h), which may provide an explanation for previous reports that bFGF can stimulate proliferation of endothelial cells, whereas VEGF can stimulate migration of endothelial cells. Our observations demonstrate that ES inhibits bFGF-stimulated phosphorylation of NL which is mediated by CK2, consequently, inhibits cell survival and proliferation.

Example Four

ES Affects Cell Motility and Adhesion via NL-Myosin Complex

Figure 6:
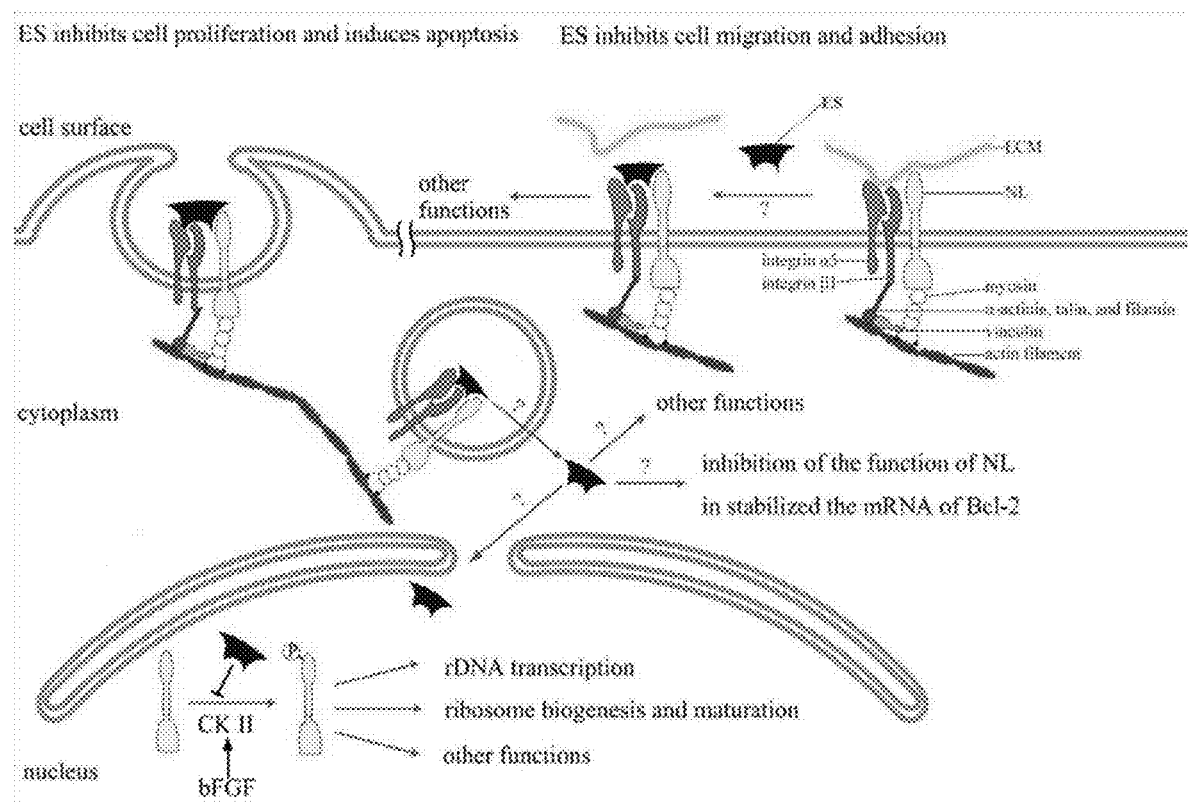
FIG. 6 provides a working model for nucleolin-mediated endostatin signal network. A big complex, which is composed of cell surface NL, integrin (such as integrin α5β1), and other proteins, is involved in the ES signal network. NL binds to myosin, which links NL and actin filaments. Similarly, integrin binds indirectly to bundles of actin filaments via the intracellular anchor proteins talin, α-actinin, filamin, and vinculin. No direct interaction can be observed between NL and integrin. ES binds to this complex competing with ECM, which leads to the decrease of cell adhesion and migration. This binding can also trigger integrin-mediated signal transduction. On the other hand, this complex can mediate ES internalization, in which myosin serves as a transporter. Subsequently, ES may be released into cytoplasm. Some ES serve as an inhibitor of NL which can stabilize the mRNA of Bcl-2, and exert other functions. The remaining ES is transported into nuclei, where it inhibits CK2-mediated NL phosphorylation as well as other down stream events.

We have demonstrated so far that NL is a novel receptor for ES in inhibiting cell migration, proliferation, and adhesion. Since integrin was also reported to be a receptor for ES, it is interesting to test whether there is an interaction between NL and integrin. Among the integrin family, integrin $\alpha5\beta1$ was reported to be the receptor for ES by Rehn et al. and Sudhakar et al., therefore, colocalization between cell surface NL and integrin $\alpha5\beta1$ was performed by indirect immunofluorescence using the mouse anti-integrin $\beta1$ and the rabbit anti-NL. Certain overlap between cell surface NL and integrin $\beta1$ was observed by laser scanning confocal microscopy (FIG. 4i-k), suggesting there are some interactions between NL and integrin $\beta1$ on cell surface. Consequently, IP with polyclonal antibodies against NL was introduced to capture the complex of NL and integrin $\beta1$. Unfortunately, integrin $\beta1$ cannot be detected in the precipitate, implying that the interaction between NL and integrin $\beta1$ is indirect. Previous studies demonstrated that myosin is involved in membrane dynamics and actin organization at cell cortex, thus affecting cell migration, adhesion, and endocytosis. We also demonstrates that NL and non-muscle myosin form a complex at cell cortex, and this complex is critical for the motility and adhesion of endothelial cells. Therefore, we speculate that ES may interfere with cell motility and adhesion mediated by NL-myosin complex. It is plausible that cell surface NL and integrin $\alpha5\beta1$ along with other proteins such as myosin form a huge complex which together serves as an integrated receptor for ES (see FIG. 6).

Example Five

The Distribution of NL Provides a Basis for the Low Toxicity of Endostatin

Figures 5G, 5H:
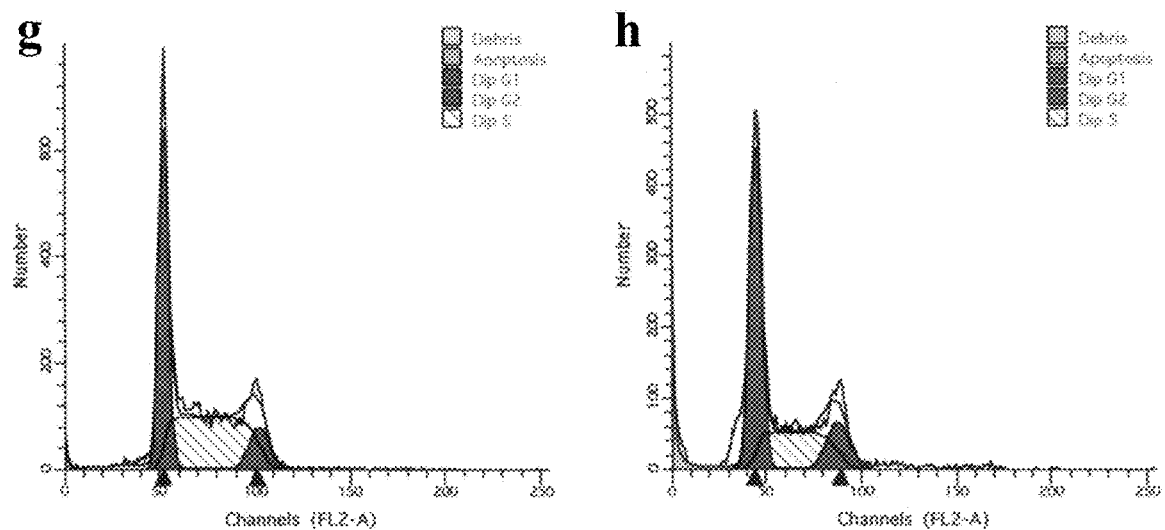
FIG. 5 shows the distribution of cell surface nucleolin depends on cell growth states. a-h, Distribution of cell surface NL on HMECs. Cell surface NL of proliferating cells and quiescent cells was detected by indirect immunofluorescence using rabbit Anti-NL. DAPI indicates all cells in the field. Scale bar, 20 µm. Cell cycle positions of proliferating cells (g) and quiescent cells (h) were detected by flow cytometry, respectively. Relatively quiescent cells were obtained by serum starvation for 24 h. i-l, Distribution of cell surface NL in tumor-bearing nude mice. Immunohistochemistry was performed as described in Methods. The blood vessels of heart (i), kidney (j), lung (k), and tumor (l) were indicated by arrows. Endothelial cells, which contain cell surface NL, were stained brown. Scale bar, 50 µm.
Figures 5I, 5J, 5K, 5L:
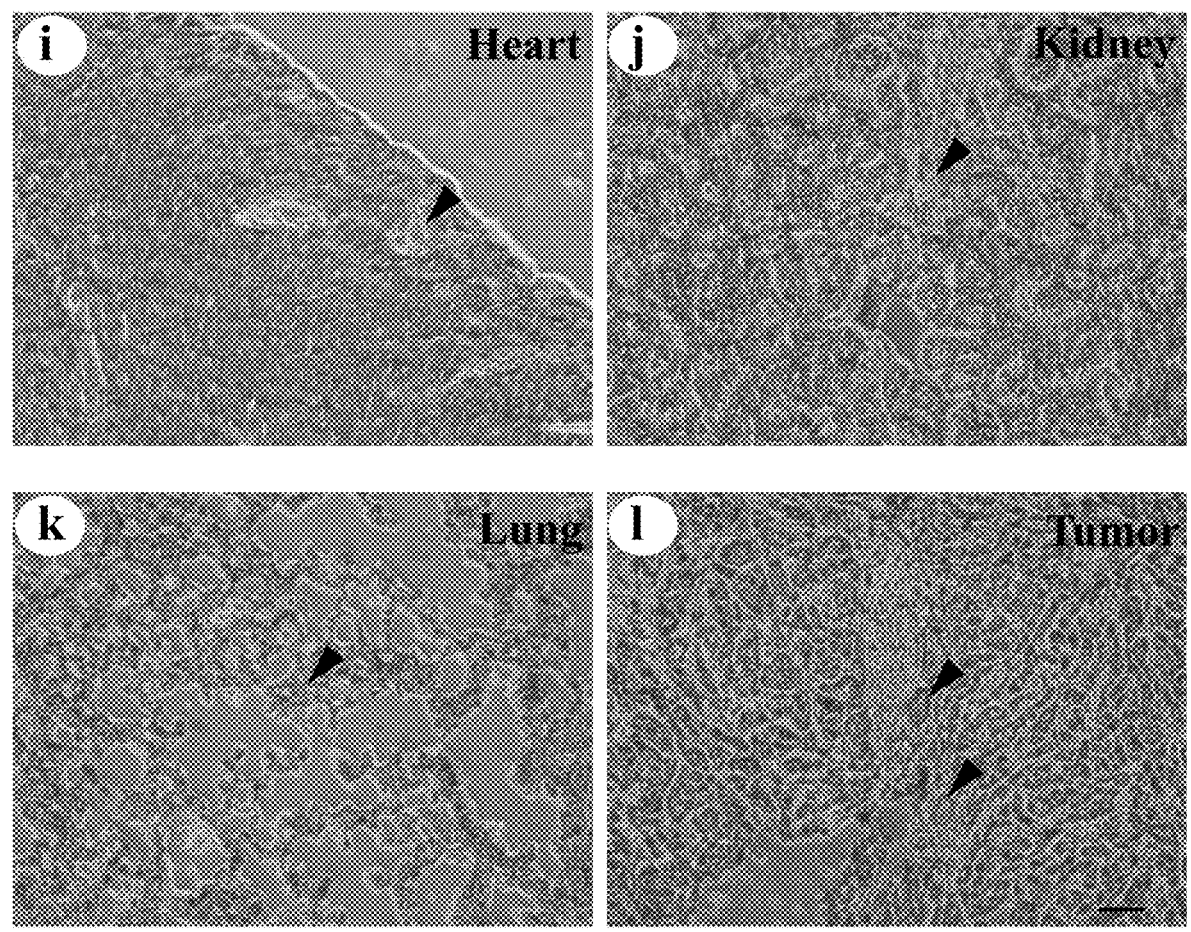

Endostatin specifically inhibits angiogenesis and tumor growth, and no toxicity on animal tests and only low toxicity on clinical trials of ES were observed. The exact molecular mechanism behind these observations is still unknown. Our conclusion that NL mediates the specific activities of ES in antiangiogenesis seems to contradict the previous report that NL is a ubiquitous protein in cells. To illuminate this paradox, the abundance of cell surface NL on HMECs at different growth states was investigated. Not surprisingly, the results show that the abundance of cell surface NL is much higher in proliferating cells than that of relatively quiescent cells (FIG. 5a-f). The relatively quiescent cells were obtained by serum starvation for 24 h, and the position of cell cycle was detected by flow cytometry (FIG. 5g-h). The results of flow cytometry show that the proportion of the G1 phase increases by 24%, and the S phase decreases by 30% after serum starvation (FIG. 5g-h). Although the cells are not completely G1-arrested, the amount of cell surface NL decreased significantly after serum starvation for 24 h. We speculate that this different abundance of cell surface NL may result in the different sensitivity of endothelial cells in response to ES.

In order to investigate whether the similar cellular phenomena can also be found on animal studies, the abundance of cell surface NL in tumor tissues and normal organs were measured. Polyclonal antibodies against NL were injected into the subcutaneous dorsal of tumor-bearing nude mice at a site remote from the inoculated tumor, and the immunohistochemistry was performed to determine the localizations of these antibodies (FIG. 5i-l). The results show that antibodies against NL are accumulated only in tumor-induced endothelial cells but not in normal tissues such as heart, kidney, and lung (FIG. 5i-l). These discoveries are perfectly consistent with the antiangiogenesis theory of Folkman: in the adult, the endothelial cells of blood vessel are in a quiescent state with a little turnover except that they are up-regulated by some endogenous angiogenic stimuli, and the proliferating endothelial cells appear in some physiological or pathological angiogenic processes such as tumor growth and metastasis. In sum, the different abundance of cell surface NL, the receptor for ES, on endothelial cells provides an explanation for the low toxicity of ES in animal tests and clinical trials: since the surface NL of endothelial cells in tumor-induced blood vessels is much more abundant than that of normal organs, ES thus specifically binds to NL and exerts its antiangiogenesis function selectively on tumor tissues; on the other hand, ES seldom bind to normal organs because they do not have much NL on their cell surface, which in turn does not induce toxicity upon ES treatment.

Example Six

Recombinant Nucleolin Modulates the Function of Endostatin in Cell Migration Assay The cDNA of NL was obtained from human microvascular endothelial cells (HMECs) using the SV total RNA isolation system and reverse transcription system (Promega) following the manufacture's protocol. The sequence of NL fusing with polyhistidine $(His)_6$ tag was amplified by PCR and then subcloned into pPIC9K (Invitrogen). Following the manufacture's protocol, this plasmid was linearized with restriction enzyme Sal I (Promega) and electrotransformed into yeast strain GS115. A stable transformant was selected using G418 and then grown in a 30° C. shaking flask for 3 days in BMMY medium (10 g/L yeast extract; 20 g/L peptone; 100 mmol/L potassium phosphate, pH 6.0; 13.4 g/L yeast nitrogen base; 40 mg/L biotin; and daily additions of methanol to the medium to yield a final concentration of 0.5%). The supernatant was obtained and the NL was purified on Ni-NTA nickel ion-affinity columns (Qiagen). We adjusted 1 L of supernatant to pH 8.0 and applied it to a column with 6 ml Ni-NTA beads. The column was washed and eluted according to the manufacturer's instructions. About 3 mg NL per liter was obtained by this procedure. Polyclonal antibodies against nucleolin were prepared with this protein.

Human umbilical vein endothelial cell (HUVEC) $(2 \times 10^4$ per well) were seeded into the upper chamber of Transwell filter (8 μm pores, Costar) with DMEM medium, 0.5% FCS, and 10 ng/ml bFGF (PeproTech EC). ES (5 μg/ml, Protgen) and rh-nucleolin (20 μg/ml), or antibodies against nucleolin (20 μg/ml) were added at the beginning of the migration assay. The PBS was added into this migration assay system as a control. The same DMEM medium and reagents were added to the lower chamber. The endothelia cells were allowed to migrate for 6 h at 37° C. and 5% $CO_2$. After fixed and stained with ethanol and Eosin, the cells migrated completely through the filter to the lower chamber were counted in five different areas under the optical microscope, and the averaged number was obtained. The results show that recombinant human nucleolin alleviated the inhibition of ES in the cell migration assay in a dose dependent manner, indicating that recombinant NL is involved in the antiangiogenesis activities of ES. Similarly, polyclonal antibodies against NL blocked the inhibition of ES on cell proliferation.

Example Seven

Acceleration of Tumor Growth when Cell Surface Nucleolin was Blocked with Antibodies against Nucleolin.

The cDNA of NL was obtained from human microvascular endothelial cells (HMECs) using the SV total RNA isolation system and reverse transcription system (Promega) following the manufacture's protocol. The sequence of NL fusing with polyhistidine $(His)_6$ tag was amplified by PCR and then subcloned into pPIC9K (Invitrogen). Following the manufacture's protocol, this plasmid was linearized with restriction enzyme Sal I (Promega) and electrotransformed into yeast strain GS115. A stable transformant was selected using G418 and then grown in a 30° C. shaking flask for 3 days in BMMY medium (10 g/L yeast extract; 20 g/L peptone; 100 mmol/L potassium phosphate, pH 6.0; 13.4 g/L yeast nitrogen base; 40 mg/L biotin; and daily additions of methanol to the medium to yield a final concentration of 0.5%). The supernatant was obtained and the NL was purified on Ni-NTA nickel ion-affinity columns (Qiagen). We adjusted 1 L of supernatant to pH 8.0 and applied it to a column with 6 ml Ni-NTA beads. The column was washed and eluted according to the manufacturer's instructions. About 3 mg NL per liter was obtained by this procedure. Polyclonal antibodies against nucleolin were prepared with this protein.

Hela cells were inoculated in the subcutaneous space of nude mice. Starting from the next day, antibodies against NL were injected slowly into the subcutaneous dorsal of mice at a site remote from the inoculated tumors every 3 days. After the seventh injection, the nude mice were killed, and the tumors were weighed and three measurements of the tumor were taken. The results of these animal tests show that the tumor growth was accelerated significantly when the cell surface nucleolin was blocked with antibodies against nucleolin. These results also demonstrated that nucleolin play a key role in regulating the tumor growth and angiogenesis.

Example Eight

Screening for NL-Specific Angiogenesis Inhibitors using ES-Ni-NTA Affinity Chromatography The cDNA of NL is obtained from human microvascular endothelial cells (HMECs). using the SV total RNA isolation system and reverse transcription system (Promega) following the manufacture's protocol. The sequence of NL fusing with polyhistidine $(His)_6$ tag is amplified by PCR and then subcloned into pPIC9K (Invitrogen). Following the manufacture's protocol, this plasmid is linearized with restriction enzyme Sal I (Promega) and electrotransformed into yeast strain GS115. A stable transformant is selected using G418 and then grown in a 30° C. shaking flask for 3 days in BMMY medium (10 g/L yeast extract; 20 g/L peptone; 100 mmol/L potassium phosphate, pH 6.0; 13.4 g/L yeast nitrogen base; 40 mg/L biotin; and daily additions of methanol to the medium to yield a final concentration of 0.5%). The supernatant is obtained and the NL was purified on Ni-NTA nickel ion-affinity columns (Qiagen). We adjust 1 L of supernatant to pH 8.0 and applied it to a column with 6 ml Ni-NTA beads. The column is washed and eluted according to the manufacturer's instructions. About 3 mg NL per liter is obtained by this procedure. This nucleolin is fixed on the Ni-NTA nickel ion-affinity columns (Qiagen) via its fusion peptide at the N-terminus. This affinity bead can be used to screen the nucleolin-binding proteins in a high-throughput manner. The nucleolin-binding proteins can be identified by PFM with MALDI-TOF. The bioactivities of these nucleolin-binding proteins in antiangiogenesis are detected with cellular experiment such as cell migration assay and cell proliferation assay as described above.

Example Nine

Col-Localization of ES and NL on the Surface of Tumor Blood Vessels

Method: Surface Plasmon Resonance

Binding kinetics was determined by SPR using a BIAcore 2000™ (Amersham Pharmacia Biotech) biosensor system. Purified ES was diluted to 100 μg/ml in 20 mM sodium acetate, pH 6.5, and covalently immobilized on the research CM5 sensor chips using the amine coupling kit (1-ethyl-3-(dimethylaminopropyl)carbodiimide, (N-hydroxysuccinimide) according to the manufacturer. ES (100 μg/ml) in sodium acetate (pH 6.5) was injected until a response difference of 9,000 units was obtained. The unreacted moieties on the surface were blocked with ethanolamine (pH 8.5; BIAcore AB). The SPR analysis between ES and NL was performed at 25° C. with a 20 μl volume of NL (62.5, 125, 250, and 500 nM) in a flow buffer HBS (10 mM Hepes, 150 mM NaCl, 3.4 mM EDTA, and 0.005% surfactant P20, pH 7.4; BIAcore AB) at a flow rate of 10 μl/min. Time course of NL, free in flow buffer, were continuously recorded as resonance units (RU). The surface was regenerated by several 10 μl pulses of 100 mM NaOH (or 100 mM HCl) flowing at 10 μl/min. The primary data were analyzed using the BIAevaluation 3.1 Software (BIAcore AB), applying a Langmuir binding model (stoichiometry of 1:1) to calculate $k_a$ (association rate constant $M^{-1}s^{-1}$), $k_b$ (dissociation rate constant, $M^{-1}$ $s^{-1}$), and $K_D$ (equilibrium constant) for the interaction of ES with NL.

The binding affinity between ES and NL was determined by real-time surface plasmon resonance (SPR), which is a rapid and sensitive method for evaluating the affinities involved in bimolecular interaction. The equilibrium constant ($K_D$) for the interaction of ES with NL is derived to be $2.32 \times 10^{-8}$ M from these curves.

Co-Localization In Vivo

Exponential growing B16/F10 mouse melanoma cells ($2 \times 10^6$ cells in 200 μl of PBS) were inoculated in the subcutaneous space of 2-mo-old Balb/c mice. The animals were used for experiments of co-localization between ES and NL in vivo 8 days after the implantation. The biotinylated ES (40 μg) and polyclonal rabbit antibodies against NL (200 μg) were injected i.v., respectively. The biotinylated ES (40 μg) and purified rabbit IgG was intravenously injected as a control. The mice were anesthetized 1 hour after the injection, perfused through the heart with 20 ml PBS, and killed. Some tissues and tumor of the mice were fixed and sectioned. The sections were detected with both TRITC-conjugated avidin (Pierce) and FITC-conjugated secondary antibodies, and were observed under the Olympus Fluoview laser scanning confocal imaging system (Olympus Inc.).

Figures 7A, 7O:
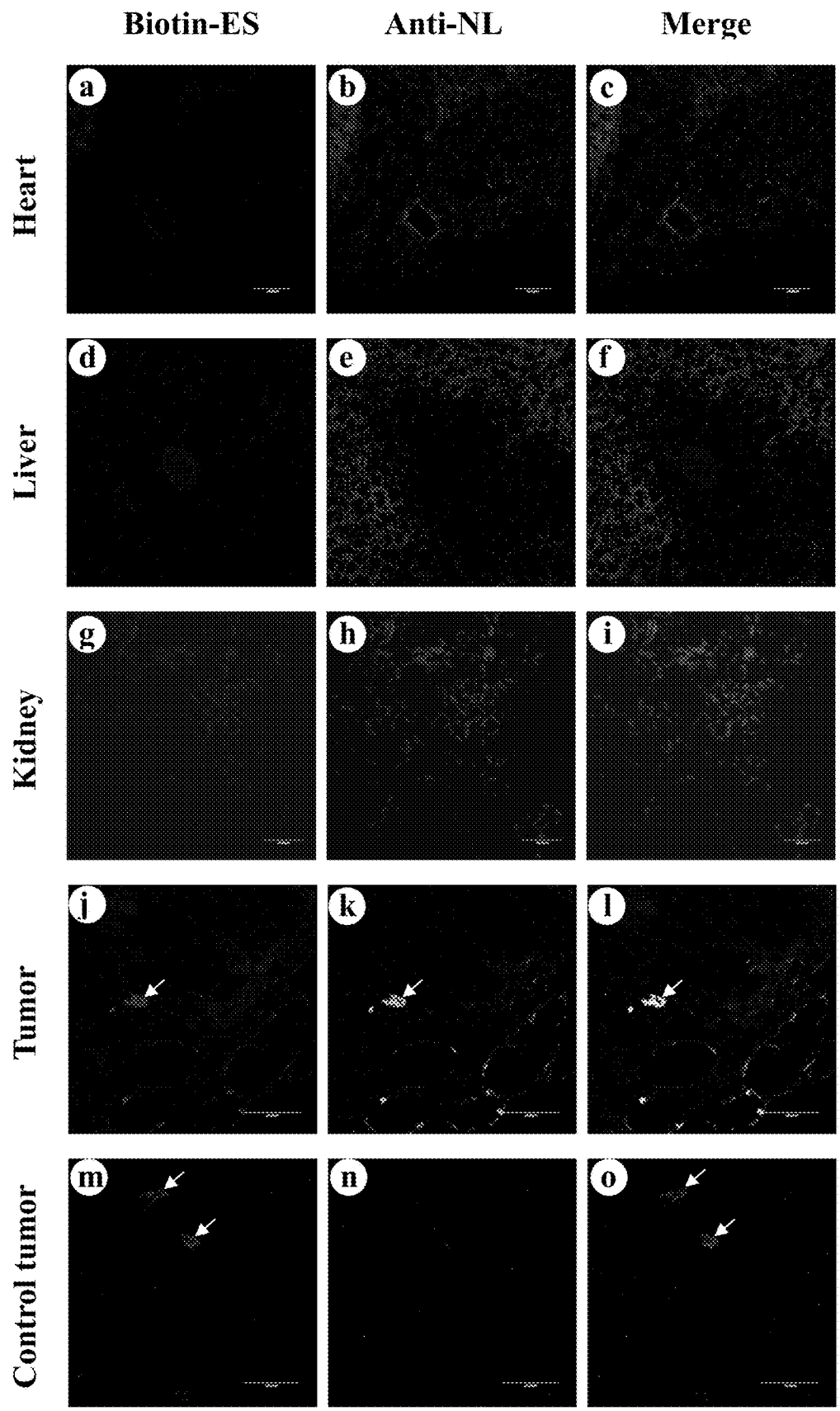
FIG. 7 shows the co-localization between ES and NL in vivo. Biotinylated ES and antibodies against NL were injected intravenously into mice bearing B16-F10 tumors. Biotinylated ES and purified rabbit IgG was injected intravenously as a control. The distribution of the biotin-labeled ES and anti-NL in heart (a-c), liver (d-f), kidney (g-i), tumor (j-l), and control tumor (m-o) were detected with both TRITC-conjugated avidin and FITC-conjugated secondary antibodies. Scale bar, 50 µm.
Figure 8:
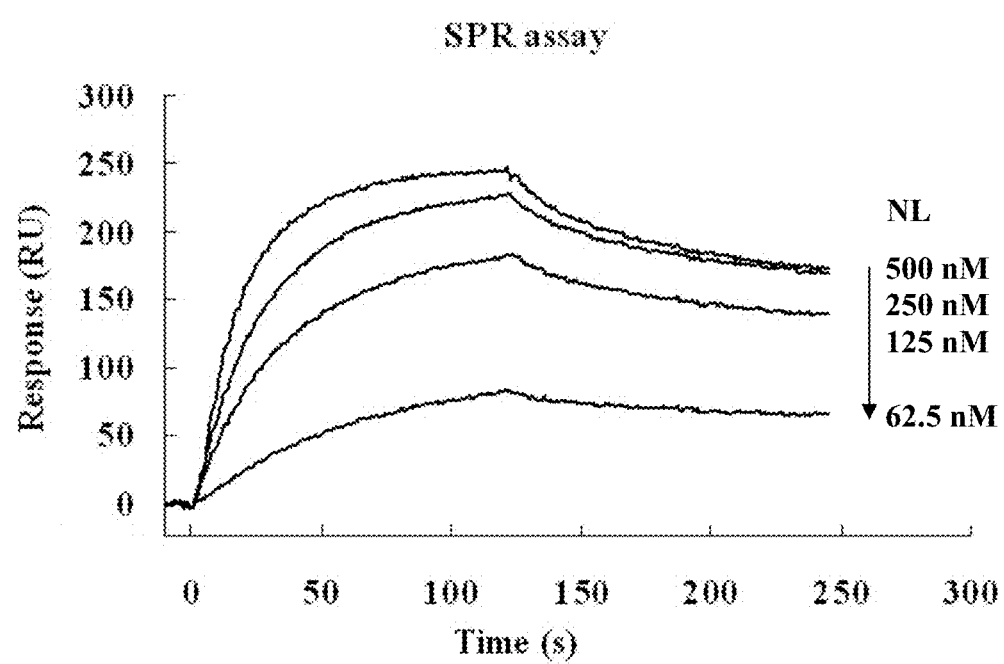
FIG. 8 shows the kinetic binding sensorgrams depicting real-time interactions between ES and NL at indicated concentrations.

Co-localization between ES and cell surface can also be observed in vivo. The biotinylated ES and antibodies against NL were injected intravenously into mice bearing B16-F10 tumors. The biotinylated ES and purified rabbit IgG was injected i.v. as a control. Tissues were collected 1 h after injection, and immunofluorescence was performed. The biotin-labeled ES and antibodies against NL selectively accumulated on the surface of tumor blood vessels (FIG. 7j-l). None of them could be detected on the blood vessels of other tissues such as heart (FIG. 7a-c), liver (FIG. 7d-f), and kidney (FIG. 7g-i). In tumor tissue, a perfect merge between biotinylated ES and antibodies against NL was observed. Control IgG was not detectable in the tumor tissues (FIG. 7m-o). These results suggest that ES and NL are co-localized on the surface of tumor blood vessels but not blood vessels of other normal tissues.

All papers, publications, literature, patents, patent applications, websites, and other printed or electronic documents referred herein, including but not limited to the references listed below, are incorporated by reference in their entirety.

REFERENCES

O'Reilly, M. S. et al. Endostatin: an endogenous inhibitor of angiogenesis and tumor growth. Cell 88, 277-285 (1997).

Boehm, T., Folkman, J., Browder, T. & O'Reilly, M. S. Antiangiogenic therapy of experimental cancer does not induce acquired drug resistance. Nature 390, 404-407 (1997).

Herbst, R. S. et al. Phase I Study of Recombinant Human Endostatin in Patients With Advanced Solid Tumors. J. Clin. Oncol. 20, 3792-3803 (2002).

Eder, J. P. Jr. et al. Phase I Clinical Trial of Recombinant Human Endostatin Administered as a Short Intravenous Infusion Repeated Daily. J. Clin. Oncol. 20, 3772-3784 (2002).

Dhanabal, M. et al. Endostatin: Yeast Production, Mutants, and Antitumor Effect in Renal Cell Carcinoma. Cancer Res. 59, 189-197 (1999).

Yamaguchi, N. et al. Endostatin inhibits VEGF-induced endothelial cell migration and tumor growth independently of zinc binding. EMBO. J. 18, 4414-4423 (1999).

Rehn, M. et al. Interaction of endostatin with integrins implicated in angiogenesis. Proc. Natl. Acad. Sci. USA 98, 1024-1029 (2001).

Dixelius, J. et al. Endostatin-induced tyrosine kinase signaling through the Shb adaptor protein regulates endothelial cell apoptosis. Blood 95, 3403-3411 (2000).

MacDonald, N. J. et al. Endostatin Binds Tropomyosin. A potential modulator of the antitumor activity of endostatin. J. Biol. Chem. 276, 25190-25196 (2001).

Karumanchi, S. A. et al. Cell surface glypicans are low-affinity endostatin receptors. Mol. Cell. 7, 811-822 (2001).

Yu, Y. et al. E-selectin is required for the antiangiogenic activity of endostatin. Proc. Natl. Acad. Sci. USA 101, 8005-8010 (2004).

Hanai, J. -i. et al. Endostatin Causes G1 Arrest of Endothelial Cells through Inhibition of Cyclin D1. J. Biol. Chem. 277, 16464-16469 (2002).

Orrick, L. R., Olson, M. O. J. & Busch, H. Comparison of Nucleolar Proteins of Normal Rat Liver and Novikoff Hepatoma Ascites Cells by Two-Dimensional Polyacrylamide Gel Electrophoresis. Proc. Natl. Acad. Sci. USA 70, 1316-1320 (1973).

Lapeyre, B., Bourbon, H. & Amalric, F. Nucleolin, the Major Nucleolar Protein of Growing Eukaryotic Cells: An Unusual Protein Structure Revealed by the Nucleotide Sequence. Proc. Natl. Acad. Sci. USA 84, 1472-1476 (1987).

Pasternack, M., Bleier, K. & McInerney, T. Granzyme A binding to target cell proteins. Granzyme A binds to and cleaves nucleolin in vitro. J. Biol. Chem. 266, 14703-14708 (1991).

Chen, C., Chiang, S. & Yeh, N. Increased stability of nucleolin in proliferating cells by inhibition of its self-cleaving activity. J. Biol. Chem. 266, 7754-7758 (1991).

Fang, S. -H. & Yeh, N. -H. The Self-Cleaving Activity of Nucleolin Determines Its Molecular Dynamics in Relation to Cell Proliferation. Exp. Cell Res. 208, 48-53 (1993).

Srivastava, M. & Pollard, H. B. Molecular dissection of nucleolin's role in growth and cell proliferation: new insights. FASEB J. 13, 1911-1922 (1999).

Ginisty, H., Sicard, H., Roger, B. & Bouvet, P. Structure and functions of nucleolin. J. Cell Sci. 112, 761-772 (1999).

Borer, R. A., Lehner, C. F., Eppenberger, H. M. & Nigg, E. A. Major nucleolar proteins shuttle between nucleus and cytoplasm. Cell 56, 379-390 (1989).

Callebaut, C. et al. Identification of V3 Loop-binding Proteins as Potential Receptors Implicated in the Binding of HIV Particles to CD4+ Cells. J. Biol. Chem. 273, 21988-21997 (1998).

Shibata, Y. et al. Nuclear Targeting by the Growth Factor Midkine. Mol. Cell Biol. 22, 6788-6796 (2002).

de Verdugo, U. et al. Characterization of a 100-kilodalton binding protein for the six serotypes of coxsackie B viruses. J. Virol. 69, 6751-6757 (1995).

Folkman, J. What is the role of endothelial cells in angiogenesis? Lab. Invest. 51, 601-604 (1984).

Marshak, D. R., Kadonaga, J. T., Burgess, R. R. & Knuth, M. W. Strategies for protein Purification and Characterization: A Laboratory Course Manual (Cold Spring Harbor Laboratory Press, New York, 1996).

Wickstrom, S. A., Alitalo, K. & Keski-Oja, J. Endostatin Associates with Lipid Rafts and Induces Reorganization of the Actin Cytoskeleton via Down-regulation of RhoA Activity. J. Biol. Chem. 278, 37895-37901 (2003).

Christian, S. et al. Nucleolin expressed at the cell surface is a marker of endothelial cells in angiogenic blood vessels. J. Cell Biol. 163, 871-878 (2003).

Gillespie, G. Y., Soroceanu, L., Manning, T. J. Jr., Gladson, C. L. & Rosenfeld, S. S. Glioma Migration Can Be Blocked by Nontoxic Inhibitors of Myosin II. Cancer Res. 59, 2076-2082 (1999).

Chavrier, P. May the force be with you: Myosin-X in phagocytosis. Nat. Cell Biol. 4, E169-71 (2002).

Wylie, S. R. & Chantler, P. D. Separate but linked functions of conventional myosins modulate adhesion and neurite outgrowth. Nat. Cell Biol. 3, 88-92 (2001).

Mehta, A. Myosin learns to walk. J. Cell Sci. 114, 1981-1998 (2001).

Deng, J. S., Ballou, B. & Hofmeister, J. K. Internalization of anti-nucleolin antibody into viable HEp-2 cells. Mol. Biol. Rep. 23, 191-195 (1996).

Bouche, G., Baldin, V., Belenguer, P., Prats, H. & Amalric, F. Activation of rDNA transcription by FGF-2: key role of protein kinase CKII. Cell Mol. Biol. Res. 40, 547-554 (1994).

Bonnet, H. et al. Fibroblast Growth Factor-2 Binds to the Regulatory beta Subunit of CK2 and Directly Stimulates CK2 Activity toward Nucleolin. J. Biol. Chem. 271, 24781-24787 (1996).

Bouche, G. et al. Basic Fibroblast Growth Factor Enters the Nucleolus and Stimulates the Transcription of Ribosomal Genes in ABAE Cells Undergoing G0 rightarrow G1 Transition. Proc. Natl. Acad. Sci. USA 84, 6770-6774 (1987).

Sudhakar, A. et al. Human tumstatin and human endostatin exhibit distinct antiangiogenic activities mediated by alpha vbeta 3 and alpha 5beta 1 integrins. Proc. Natl. Acad. Sci. USA 100, 4766-4771 (2003).

Folkman, J. Angiogenesis in cancer, vascular, rheumatoid and other disease. Nat. Med. 1, 27-31 (1995).

Sasaki, T., Hohenester, E. & Timpl, R. Structure and function of collagen-derived endostatin inhibitors of angiogenesis. IUBMB Life 53, 77-84 (2002).

Sasaki, T. et al. Structural basis and potential role of heparin/heparan sulfate binding to the angiogenesis inhibitor endostatin. EMBO J. 18, 6240-6248 (1999).

Kreuger, J. et al. Role of heparan sulfate domain organization in endostatin inhibition of endothelial cell function. EMBO J. 21, 6303-6311 (2002).

Li, B., Wu, X., Zhou, H., Chen, Q. & Luo, Y. Acid-induced unfolding mechanism of recombinant human endostatin. Biochemistry 43, 2550-2557 (2004).

Wu, X., Huang, J., Chang, G. & Luo, Y. Detection and characterization of an acid-induced folding intermediate of endostatin. Biochem. Biophys. Res. Commun. 320, 973-978 (2004).

Meredith J. E. Jr., Fazeli. B. & Schwartz M. A. The extracellular matrix as a cell survival factor. Mol. Biol. Cell 4, 953-61 (1993).

Dhanabal, M. et al. Endostatin Induces Endothelial Cell Apoptosis. J. Biol. Chem. 274, 11721-11726 (1999).

Sengupta, T. K., Bandyopadhyay, S., Fernandes, D. J. & Spicer, E. K. Identification of Nucleolin as an AU-rich Element Binding Protein Involved in bcl-2 mRNA Stabilization. J. Biol. Chem. 279, 10855-10863 (2004).

Maeshima, Y., Colorado, P. C. & Kalluri, R. Two RGD-independent alpha vbeta 3 Integrin Binding Sites on Tumstatin Regulate Distinct Anti-tumor Properties. J. Biol. Chem. 275, 23745-23750 (2000).

Sui, G. et al. A DNA vector-based RNAi technology to suppress gene expression in mammalian cells. Proc. Natl. Acad. Sci. USA 99, 5515-5520 (2002).

Sastry, S. K. & Burridge, K. Focal Adhesions: A Nexus for Intracellular Signaling and Cytoskeletal Dynamics. Exp. Cell Res. 261, 25-36 (2000).

We claim:

1. A method of determining the susceptibility of a subject with a tumor to endostatin therapy, comprising:
   (a) performing an immunoassay on a tumor tissue sample from the subject for the presence of cell surface nucleolin on endothelial cells in tumor blood vessels;
   (b) determining if the subject is susceptible to endostatin therapy based on the result of the immunoassay, wherein the presence of cell surface nucleolin on endothelial cells in tumor blood vessels of the tumor tissue sample indicates that the subject is susceptible to endostatin therapy; and
   (c) administering, to the subject that is determined to be susceptible to endostatin therapy, endostatin in an amount effective to inhibit angiogenesis.

2. The method of claim 1, wherein the immunoassay is performed with an antibody that specifically binds to nucleolin.

3. The method of claim 2, wherein the formation of a complex between the antibody and nucleolin is detected.

4. The method of claim 2, wherein the antibody is a monoclonal antibody.

5. The method of claim 1, wherein the subject is a mammal.

6. The method of claim 5, wherein the mammal is a human.

7. The method of claim 1, wherein the endothelial cells are capillary endothelial cells.

8. The method of claim 1, wherein the tumor blood vessels are angiogenic blood vessels.

9. The method of claim 8, wherein the endothelial cells are proliferating endothelial cells.

10. A method of treating a subject having a tumor comprising:
    (a) selecting a subject that is determined to be susceptible to endostatin therapy using the method of claim 1; and
    (b) administering to the subject endostatin in an amount effective to inhibit angiogenesis.

11. The method of claim 10, wherein the tumor is a cancer.

12. The method of claim 10, wherein the subject is a mammal.

13. The method of claim 10, wherein the subject is a human.

14. A method of determining the susceptibility of a subject with a tumor to endostatin therapy, comprising:
    (a) performing an immunoassay on a tumor tissue sample from said subject to detect the presence of nucleolin on the surface of endothelial cells;

(b) identifying the subject is susceptible to endostatin therapy based on the result of the immunoassay, wherein increased level of nucleolin on the cell surface of said endothelial cells in tumor blood vessels compared to a level of nucleolin in a control sample indicates that the subject is susceptible to endostatin therapy; and (c) administering, to the subject that is determined to be susceptible to endostatin therapy, endostatin in an amount effective to inhibit angiogenesis.

15. The method according to claim 14, wherein the control sample is a normal heart tissue, lung tissue, or kidney tissue.

* * * * *

UNITED STATES PATENT AND TRADEMARK OFFICE
CERTIFICATE OF CORRECTION

PATENT NO. : 11,434,288 B2  
APPLICATION NO. : 12/412065  
DATED : September 6, 2022  
INVENTOR(S) : Yongzhang Luo Page 1 of 1

It is certified that error appears in the above-identified patent and that said Letters Patent is hereby corrected as shown below:

On the Title Page

Item (73) reads: "Protogen Ltd., Beijing (CN); Tsinghua University, Beijing (CN)"  
Should read: --Tsinghua University, Beijing (CN); Protogen Ltd., Beijing (CN)--

Signed and Sealed this  
Seventh Day of November, 2023

Katherine Kelly Vidal  
*Director of the United States Patent and Trademark Office*